(12) United States Patent
Jinno

(10) Patent No.: US 9,788,847 B2
(45) Date of Patent: Oct. 17, 2017

(54) MEDICAL MANIPULATOR

(75) Inventor: Makoto Jinno, Tokyo (JP)

(73) Assignee: Karl Storz GmbH & Co. KG, Tuttlingen (DE)

( * ) Notice: Subject to any disclaimer, the term of this patent is extended or adjusted under 35 U.S.C. 154(b) by 783 days.

(21) Appl. No.: 13/617,573

(22) Filed: Sep. 14, 2012

(65) Prior Publication Data
US 2013/0012959 A1 Jan. 10, 2013

Related U.S. Application Data

(63) Continuation of application No. PCT/JP2011/055222, filed on Mar. 7, 2011.

(30) Foreign Application Priority Data

Mar. 15, 2010 (JP) ................................ 2010-057400

(51) Int. Cl.
A61B 17/29 (2006.01)
A61B 34/30 (2016.01)
(Continued)

(52) U.S. Cl.
CPC .............. A61B 17/29 (2013.01); A61B 34/30 (2016.02); A61B 34/37 (2016.02); A61B 34/71 (2016.02);
(Continued)

(58) Field of Classification Search
CPC ................ A61B 17/29; A61B 19/2203; A61B 2019/2242; A61B 2019/2276; A61B 2019/2223; A61B 2017/0046; A61B 2017/00398; A61B 2017/2939; A61B 2017/2919; A61B 2017/2925; A61B 2017/2923
(Continued)

(56) References Cited

U.S. PATENT DOCUMENTS

2005/0222587 A1 10/2005 Jinno et al.
2006/0095143 A1* 5/2006 Sunaoshi ............... A61B 19/22
700/3
(Continued)

FOREIGN PATENT DOCUMENTS

EP 1 813 205 A1 8/2007
EP 2 095 778 A1 9/2009
(Continued)

OTHER PUBLICATIONS

Extended European Search Report dated Nov. 7, 2013, issued by the European Patent Office in the corresponding European Application No. 11756113.4. (5 pages).
(Continued)

Primary Examiner — Corrine McDermott
Assistant Examiner — Tin Nguyen
(74) Attorney, Agent, or Firm — Whitmyer IP Group LLC

(57) ABSTRACT

A medical manipulator includes a trigger lever operated by hands, a shaft that extends from a body in which the trigger lever is provided, and a tip operating unit that is provided at a tip of the shaft. The tip operating unit includes an end effector to which the operation of the trigger lever is mechanically transmitted and in which the operation is performed, and a detection mechanism that detects an operation state of the first input unit.

16 Claims, 21 Drawing Sheets

(51) Int. Cl.
*A61B 34/37* (2016.01)
*A61B 17/00* (2006.01)
*A61B 34/00* (2016.01)

(52) U.S. Cl.
CPC ............ *A61B 2017/0046* (2013.01); *A61B 2017/00398* (2013.01); *A61B 2017/2919* (2013.01); *A61B 2017/2923* (2013.01); *A61B 2017/2925* (2013.01); *A61B 2017/2939* (2013.01); *A61B 2034/742* (2016.02)

(58) Field of Classification Search
USPC ................................................ 606/205, 130
See application file for complete search history.

(56) References Cited

U.S. PATENT DOCUMENTS

| | | |
|---|---|---|
| 2006/0278680 A1 | 12/2006 | Viola et al. |
| 2008/0164296 A1 | 7/2008 | Shelton et al. |
| 2009/0030428 A1* | 1/2009 | Omori et al. ............... 606/130 |
| 2009/0110533 A1 | 4/2009 | Jinno |
| 2009/0112229 A1 | 4/2009 | Omori et al. |
| 2009/0216248 A1 | 8/2009 | Uenohara et al. |

FOREIGN PATENT DOCUMENTS

| | | |
|---|---|---|
| JP | 2003-144448 A | 5/2003 |
| JP | 2004-105451 A | 4/2004 |
| JP | 2007-130485 A | 5/2007 |
| JP | 2008-212638 A | 9/2008 |
| JP | 2009045428 A | 3/2009 |
| JP | 2009-106606 A | 5/2009 |
| JP | 2009-107095 A | 5/2009 |
| JP | 2009226194 A | 10/2009 |
| WO | 2009089539 A1 | 7/2009 |

OTHER PUBLICATIONS

International Search Report (PCT/ISA/210) dated Mar. 29, 2011, by the Japanese Patent Office as the International Searching Authority for International Application No. PCT/JP2011/055222.

* cited by examiner

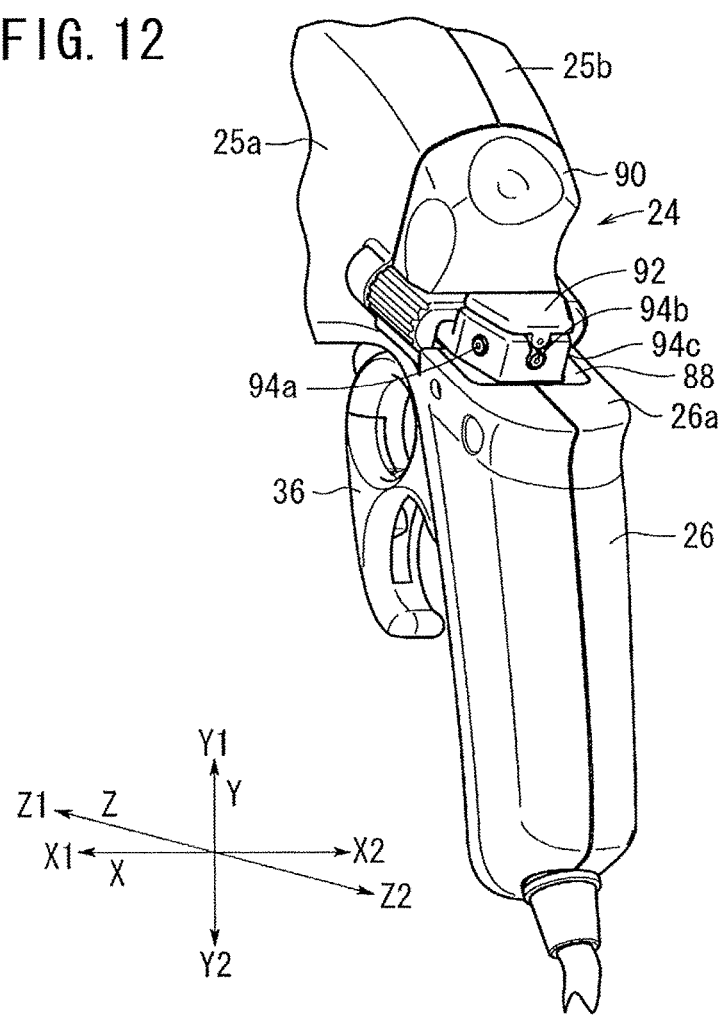

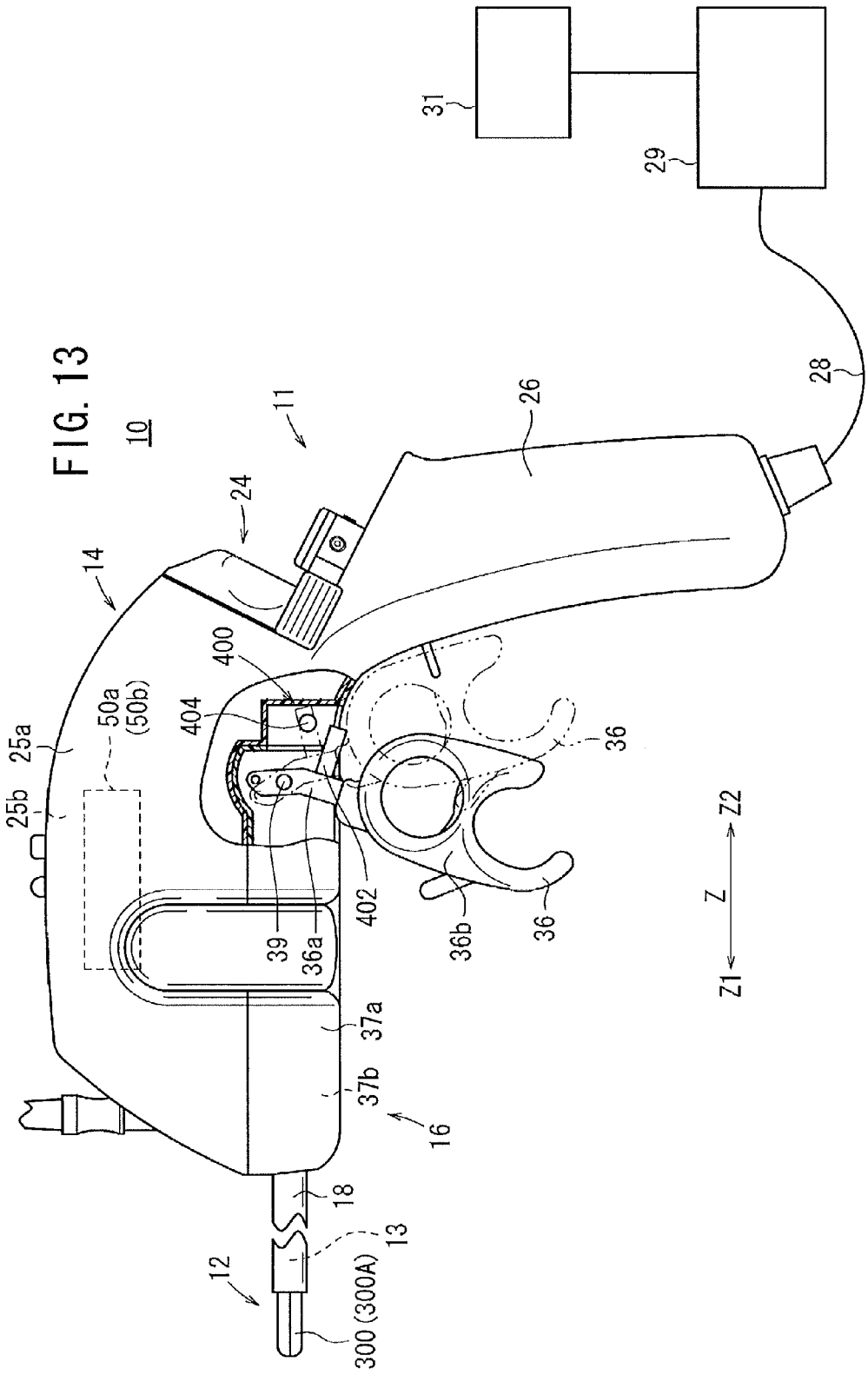

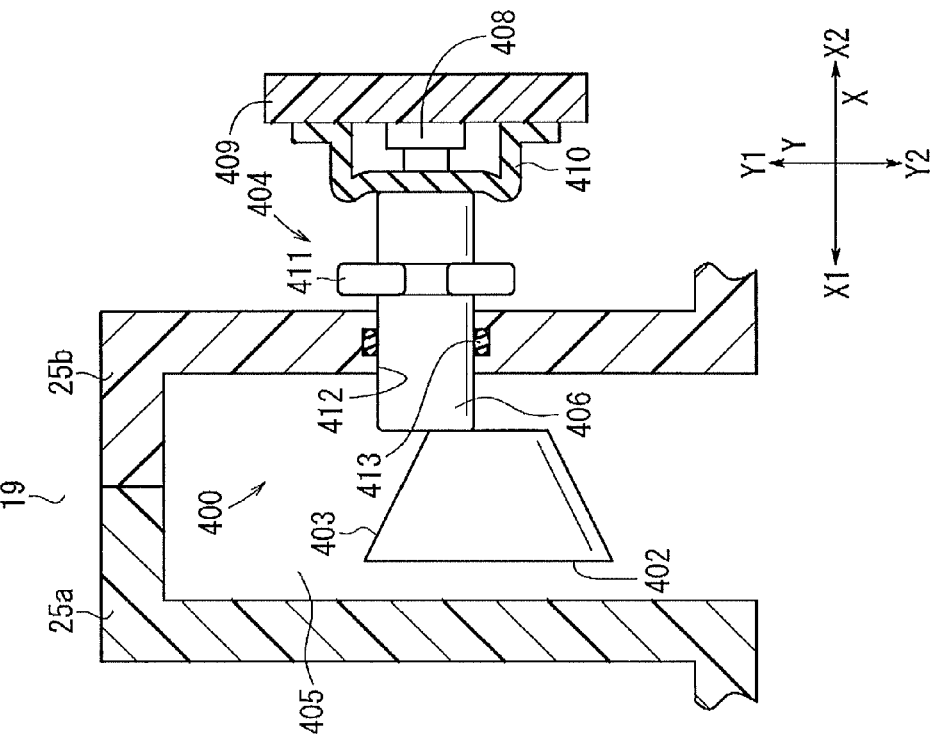
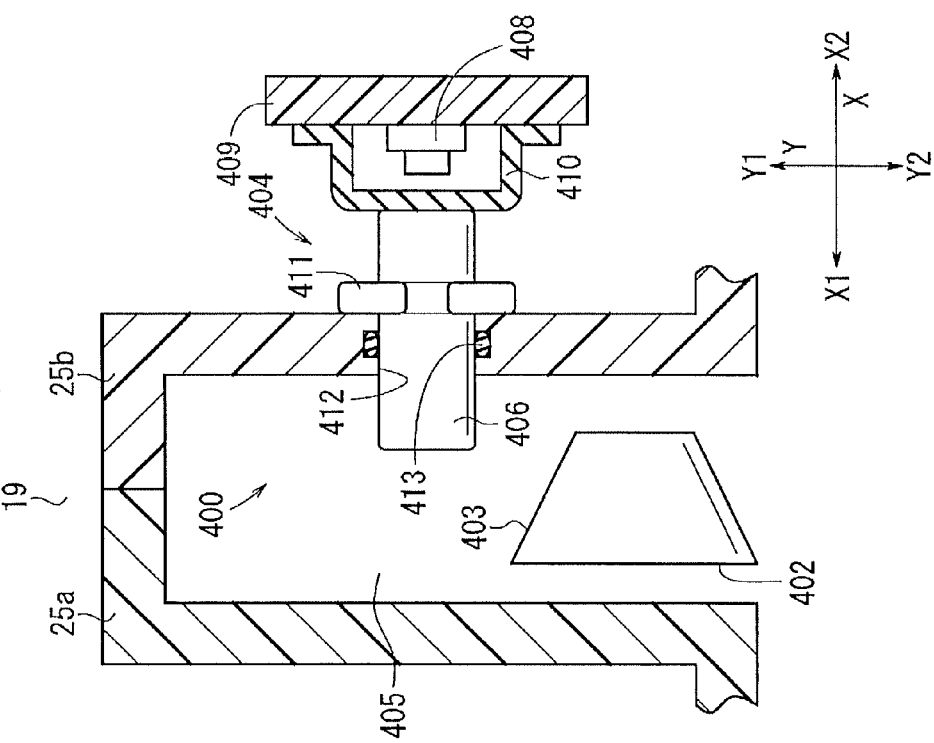

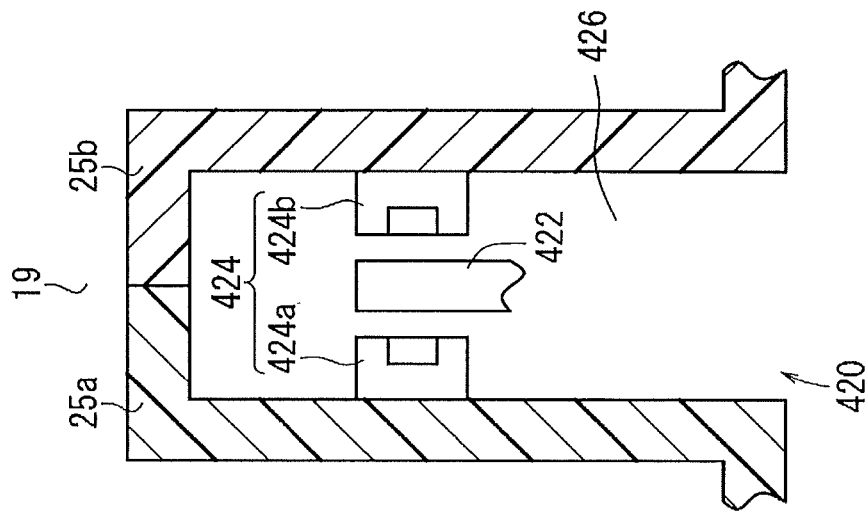
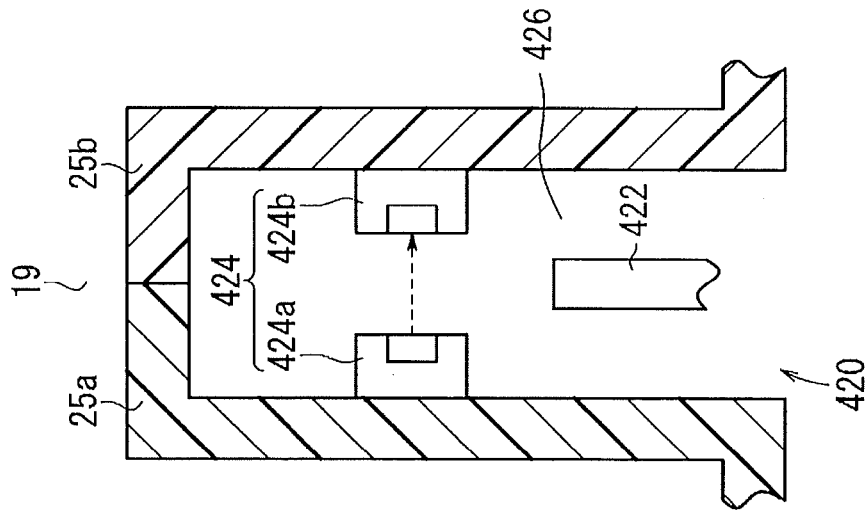

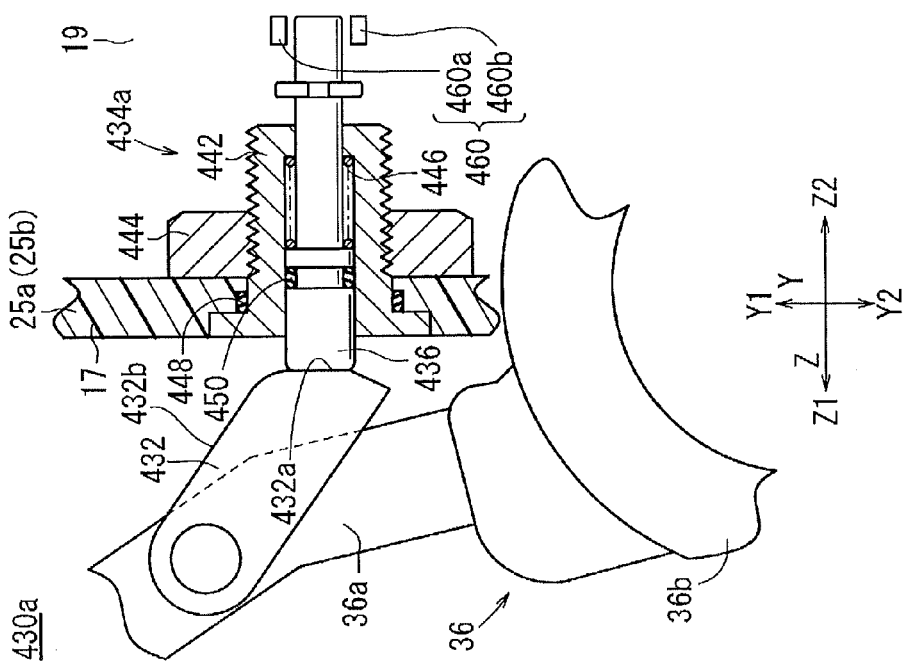
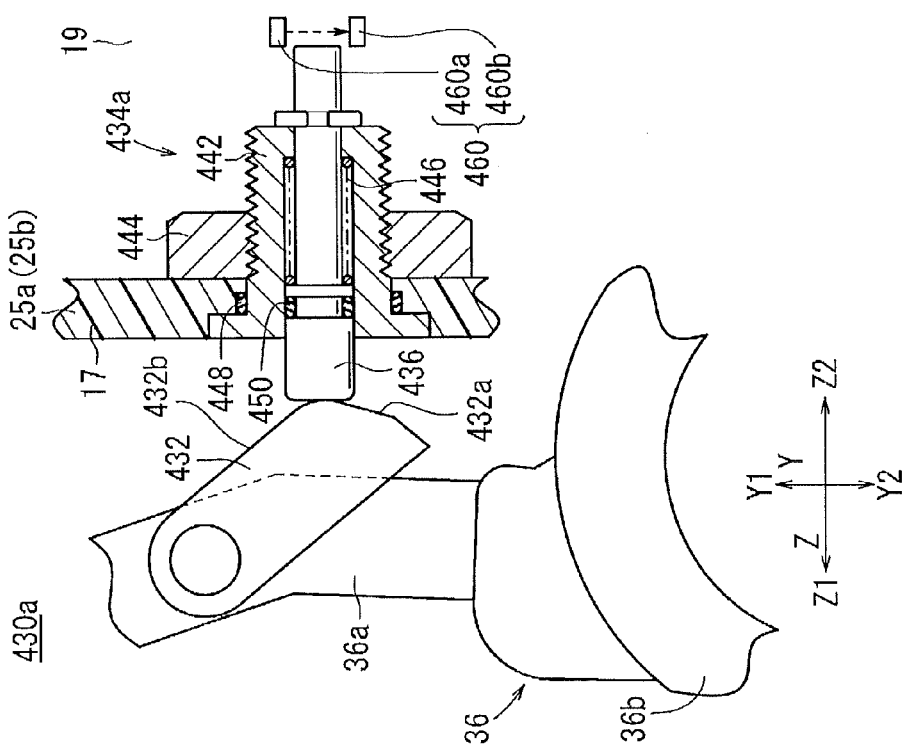

MEDICAL MANIPULATOR

CROSS REFERENCES TO RELATED APPLICATIONS

This application is a continuation of International Application No. PCT/JP2011/055222 filed on Mar. 7, 2011 and claims priority to Japanese Patent Application JP2010-057400 filed in the Japanese Patent Office on Mar. 15, 2010, the entire content of both of which is incorporated herein by reference.

TECHNICAL FIELD

The present disclosure generally pertains to a medical manipulator. More particularly, the disclosure relates to a medical manipulator that includes an input unit which is operated by hands and a tip operating unit having an end effector operated based on the operation of the input unit.

BACKGROUND DISCUSSION

In endoscopic surgery (also referred to as "laparoscopic surgery"), plural holes are drilled into the abdomen of a patient, and after a trocar (cylindrical instrument) is inserted into the holes, a laparoscope (camera) and a plurality of forceps are inserted into a body cavity through each trocar. Grippers, scissors, or blades of an electrosurgical knife, for gripping biological tissues are mounted on the tips of the forceps as an end effector. If the laparoscope and the forceps are inserted into the body cavity, an operator operates the forceps while viewing a state of the inner portion of the abdominal cavity, which is shown on the monitor connected to the laparoscope. Since the surgical procedure does not require a laparotomy, the patient burden is decreased, which reduces the number of days for postoperative recovery and leaving the hospital.

General forceps that do not have a joint at the tip, and forceps that have a plurality of joints at the tip and change a posture of the tip are called a medical manipulator. (See for example, Japanese Patent Application JP-A-2004-105451). With the medical manipulator, an operation having a relatively high degree of freedom can be performed in the body cavity. In addition, the manipulation is relatively easier and applicable cases are increased with the medical manipulator. The medical manipulator disclosed in JP-A-2004-105451 includes a working unit that includes a tip operating unit having an end effector and a joint and an operating unit having a drive mechanism for driving the tip operating unit. The drive mechanism includes an actuator for changing the posture of the tip operating unit and an actuator for opening and closing the end effector and drives each of the actuators according to the operation with respect to an operation input unit that is provided in the operating unit, and the tip operation unit is operated.

When the operation is mechanically transmitted by hands and the opening and closing of the tip are performed in general with forceps that do not have a joint at the tip, the operator can perceive a gripping force acting on the tip. However, in the medical manipulator of JP-A-2004-105451, since all operations of the tip operating unit are performed by the driving of the actuator, an operator cannot directly perceive the gripping force that acts on the tip operating unit.

SUMMARY

Thus, a medical manipulator capable of allowing the gripping force that acts on the tip operating unit to be directly perceived is desirable. One aspect of the disclosure here involves a medical manipulator in which an operation to an input unit (for example, trigger lever) through hands is performed by being mechanically transmitted via a transmitting member such as a wire in the opening and closing operation of the end effector provided in the tip operating unit while the posture change of the tip operating unit is performed by the driving of the actuator, for example, a hybrid type configuration in which an electric drive and a manual drive are combined.

If frequency or a use state of the operation of the tip operating unit (posture change or opening and closing operation of end effector) is ascertained, the material ascertained is analyzed, which can be used to predict life spans of mechanisms or members that configure the working unit. In the above-disclosed hybrid type medical manipulator, drive information of the actuator is electrically detected by an encoder, and the frequency of use or a use state of the mechanism that performs the posture change of the tip operating unit can be ascertained. However, since the end effector is not driven by the actuator but is operated due to the fact that the operation through hands is mechanically transmitted via the transmitting member, it is generally not possible to detect the operation frequency or a use state of the end effector and the drive mechanism.

According to an aspect, a medical manipulator is disclosed, which is capable of detecting an operation frequency or the use state of an end effector and a drive mechanism in the medical manipulator that includes the end effector in which an operation of an input unit is mechanically transmitted and performed.

According to another aspect, a medical manipulator includes a first input unit that is operated by hands and a shaft that extends from a body in which the first input unit is provided. A tip operating unit is provided at a tip of the shaft and includes an end effector to which an operation of the first input unit is mechanically transmitted and in which the operation is performed, and a detection mechanism that detects an operation state of the first input unit.

According to a further aspect, since the operation state of the first input unit is detected by the detection mechanism, for example, ascertainment and analysis of an operation frequency or a use state of the first input unit can be performed based on the operation state, and according to the analysis, a life span prediction of the mechanism that mechanically transmits a force based on the first input unit or the operation of the first input unit can be performed.

In the medical manipulator, the detection mechanism detects that the first input unit reaches a predetermined position.

Since the first input unit reaching the predetermined position (for example, the end of the movable range or the vicinity of the end of the movable range) is detected by the detection mechanism, the frequency of use of the first input unit can be ascertained based on the detection result.

In the medical manipulator, the detection mechanism detects that the first input unit reaches a predetermined position at each of a plurality of predetermined positions in a movable range of the first input unit.

Since the reaching of the first input unit is detected at the plurality of positions, a more detailed use state can be ascertained, and reliability of the lift span prediction can be improved.

In the medical manipulator, the detection mechanism detects a position in an operation direction of the first input unit. Because the position in the operation direction of the first input unit is detected, the operation frequency of the first input unit can be ascertained, the use state can be ascertained in detail, and the reliability of the life span prediction can be improved.

In the medical manipulator, the tip operating unit includes a posture change mechanism that changes a posture of the end effector with respect to the shaft; the medical manipulator further includes an operating unit that includes a second input unit that is operated by hands, a grip handle that is gripped by hands, and a drive source that drives the posture change mechanism based on an operation of the second input unit. A working unit includes the tip operating unit, the shaft, and the first input unit and can be attached to and detached from the operating unit. A driving force of the drive source is mechanically transmitted to the posture change mechanism in a state where the working unit is mounted on the operating unit, which changes a posture of the end effector. The detection mechanism includes a protrusion piece for detection that is provided in the first input unit and a detecting unit that is provided in the operating unit. The detecting unit detects the protrusion piece for detection in the state where the working unit is mounted on the operating unit, and detects that the first input unit reaches the predetermined position.

Electronic equipment for operating the tip operation unit need not be provided in the working unit, and electronic equipment for detecting the operation state of the first input unit need not be provided in the working unit, and so the working unit can be cleaned relatively easily and sterilized.

In the medical manipulator, the tip operating unit includes a posture change mechanism that changes a posture of the end effector with respect to the shaft. The medical manipulator further includes an operating unit that includes a second input unit that is operated by hands, a grip handle that is gripped by hands, and a drive source that drives the posture change mechanism based on an operation of the second input unit. A working unit that includes the tip operating unit, the shaft, and the first input unit and can be attached to and detached from the operating unit. A driving force of the drive source is mechanically transmitted to the posture change mechanism in the state where the working unit is mounted on the operating unit, which changes a posture of the end effector; and the detection mechanism includes, a drive element that is operated along with the first input unit, a driven element that is provided in the operating unit and operates in conjunction with the drive element in a state where the working unit is mounted on the operating unit, and a detecting unit that detects a position of an operation direction of the driven element.

Since the electronic equipment for operating the tip operation unit need not be provided in the working unit, and the electronic equipment for detecting the operation state of the first input unit need not be provided in the working unit, the working unit can be cleaned relatively easily and sterilized.

In the medical manipulator, the first input unit is a trigger lever that is operated to rotate, and the drive element is a first gear portion that includes teeth which extend in a circumferential direction around a rotation axial center of the trigger lever. The driven element is a second gear portion that is rotatably provided in the operating unit and meshes with the first gear portion in the state where the working unit is mounted on the operating unit; and the detecting unit is a rotation detector that detects a rotation angle of the second gear portion. The operation angle of the trigger lever can be detected by a relatively simple configuration.

In the medical manipulator, a rotation axial center of the trigger lever and a rotation axial center of the second gear portion are positioned so as to be off-set from each other in an extension direction of the shaft in the state where the working unit is mounted on the operating unit.

When the working unit is mounted on the operating unit, since the first gear portion provided in the working unit and the second gear portion provided in the operating unit are off-set from each other in the front and rear direction (axial line direction of shaft), the meshing operation between the first gear portion and the second gear portion can be relatively smoothly performed. The mounting operation of the working unit on the operating unit can be relatively smoothly performed.

In the manipulator, the tip operating unit includes a conversion mechanism that converts an operation based on the operation of the first input unit to an operation of the end effector; the posture change mechanism includes a main shaft member in which a first rotation body that is rotated by a first actuator via a first transmitting member inserted into the shaft is provided and which can rotate about a tilt shaft which is non-parallel to an axial line of the shaft. A second rotation body that is rotated by a second actuator via a second transmitting member inserted into the shaft, and a third rotation body that is driven by the second rotation body and is supported to the main shaft member so as to rotate about the roll axis in an extension direction of the end effector. The main shaft member driven by the first transmitting member rotates about the tilt shaft, which performs a tilting operation of the end effector; the second rotation body driven by the second transmitting member rotates the third rotation body about the roll axis, which performs a roll operation of the end effector. The medical manipulator further includes a controller that controls the first actuator and the second actuator; and the controller controls the first actuator so as to help prevent or help suppress the generation of the tilting operation due to the roll operation according to the operation state of the first input unit based on a detection result from the detection mechanism.

Since the first actuator is controlled in addition to the operation state of the first input unit, even when the rotation resistance of the third rotation body is increased due to the operation state of the first input unit, the generation of the tilting operation due to the roll operation can be prevented or suppressed. Thereby, trajectory accuracy or positioning accuracy of the tip operating unit at the time of the roll operation can be improved.

In the medical manipulator, the end effector is configured of an opening and closing mechanism; and when the controller performs the control for the roll operation, in a case where the first input unit is positioned at the end of the movable range or the vicinity of the end of the movable range, a compensation control corresponding to the increase of the rotation resistance of the third rotation body is performed with respect to the first actuator so as to help prevent or help suppress the generation of the tilting operation.

Even when the rotation resistance of the third rotation body is increased due to the operation of the first input unit, the trajectory accuracy or the positioning accuracy of the tip operating unit at the time of the roll operation can be improved.

According to another aspect, a medical manipulator includes a first input unit that is operated by hands and a shaft that extends from a body in which the first input unit is provided. A tip operating unit that is provided at a tip of the shaft and includes an end effector to which an operation of the first input unit is mechanically transmitted and in which the operation is performed and a detection mechanism detects an operation state of the first input unit.

According to a further aspect, a medical manipulator is disclosed, which includes a trigger lever that is operated by hands, and a shaft that extends from a body in which the trigger lever unit is provided. A tip operating unit that is provided at a tip of the shaft and includes an end effector to which an operation of the trigger lever is mechanically transmitted and in which the operation is performed, and a detection mechanism that detects an operation state of the trigger lever.

Another aspect involves a medical manipulator which includes a first input unit that is operated by hands, and a shaft that extends from a body in which the first input unit is provided. A tip operating unit that is provided at a tip of the shaft and includes an end effector to which an operation of the first input unit is mechanically transmitted and in which the operation is performed, and a detection mechanism that detects a position in an operation direction of the first input unit.

BRIEF DESCRIPTION OF DRAWINGS

FIG. 12 is a perspective view in which a portion of a composite input unit and a peripheral portion of the composite input unit of the medical manipulator are omitted.

FIG. 13 is a side view in which a portion of the medical manipulator that includes a detection mechanism according to a first example is omitted.

FIG. 14A is a schematic view of the detection mechanism according to the first example in a state where the trigger lever is pushed out.

FIG. 14B is a schematic view of the detection mechanism according to the first example in a state where the trigger lever is pulled.

FIG. 15A is a schematic view of a detection mechanism according to a second example in the state where the trigger lever is pushed out.

FIG. 15B is a schematic view of the detection mechanism according to the second example in the state where the trigger lever is pulled.

FIG. 18A is a cross-sectional side view of a detection mechanism according to a fourth example in the state where the trigger lever is pushed out.

FIG. 18B is a cross-sectional side view of the detection mechanism according to the fourth example in the state where the trigger lever is pulled.

DETAILED DESCRIPTION

In accordance with an aspect, a medical manipulator (hereinafter, referred to as a "manipulator") will be disclosed with reference to the accompanying drawings.

Figure 1:
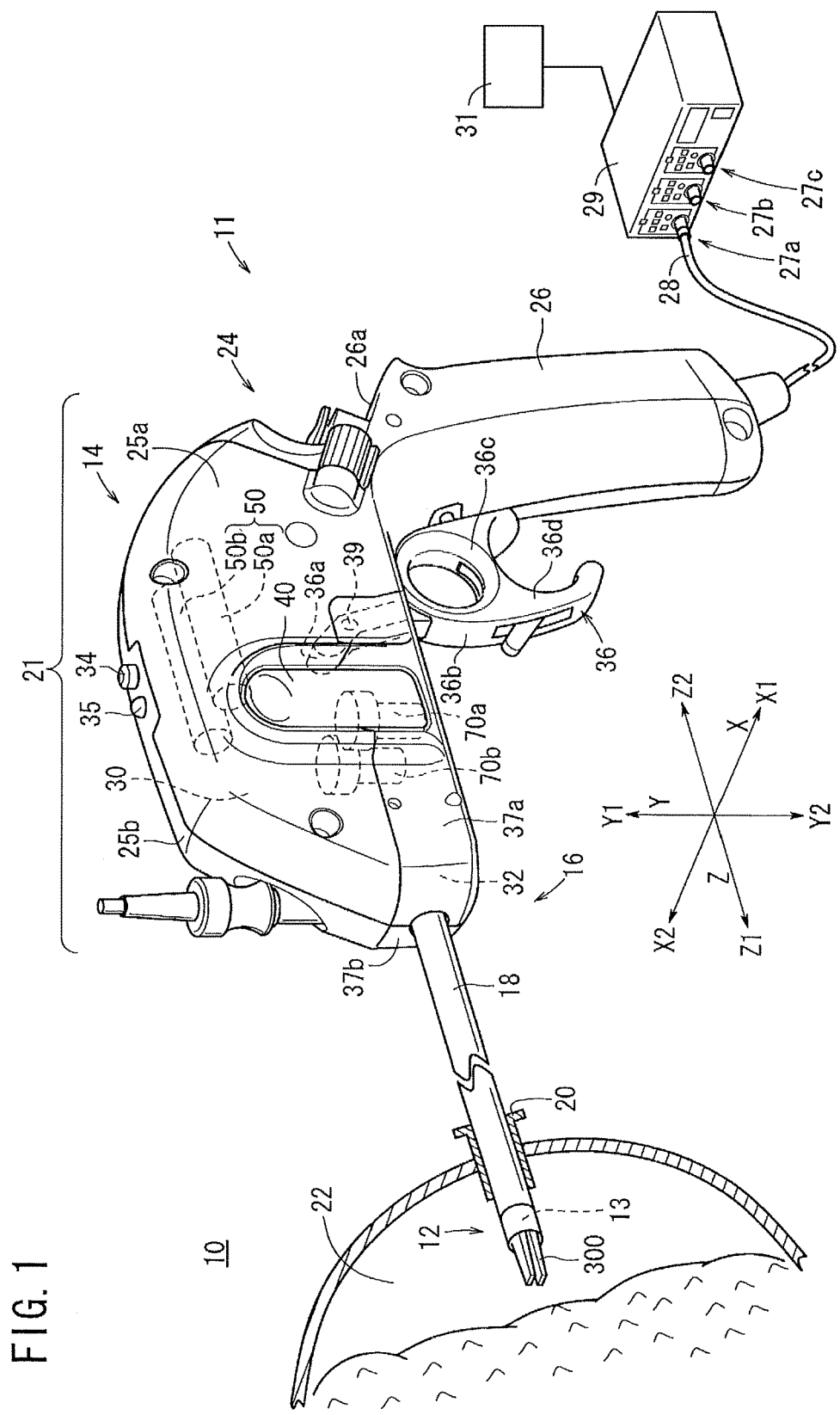
FIG. 1 is a perspective view of a medical manipulator according to a first example.

First, a medical manipulator 10 according to an aspect will be disclosed with reference to FIG. 1. The manipulator 10 is a medical instrument that grips a portion of a living body or contacts the living body through a tip operating unit 12 provided at a tip of the manipulator and performs a predetermined processing, and in general, is also referred to as gripping forceps, or a needle drive (needle holder).

The manipulator 10 includes a manipulator main body 11 that configures a medical instrument and a controller 29 that is connected to the manipulator main body 11 via a cable 28. The manipulator main body 11 includes a body 21, a shaft 18 that extends from the body 21, and a tip operating unit 12 that is provided in the tip of the shaft 18.

In descriptions hereinafter, an extension direction of the shaft 18 is defined as a Z direction, the front side (tip side) of the shaft 18 is defined as a Z1 direction, and the rear side (base side) of the shaft is defined as a Z2 direction. In addition, a direction that is perpendicular to the Z direction and is left and right directions based on the manipulator main body 11 when the manipulator main body 11 has the posture of FIG. 1 is defined as an X direction, the left side direction of the manipulator main body 11 is defined as an X1 direction, and the right side direction of the manipulator body 11 is defined as an X2 direction. Moreover, a direction that is perpendicular to the Z direction and is up and down directions based on the manipulator main body 11 when the manipulator main body 11 has the posture of FIG. 1 is defined as a Y direction, the up direction of the manipulator main body is defined as a Y1 direction, and the down direction of the manipulator main body is defined as a Y2 direction.

In addition, unless otherwise noted, these direction descriptions are expressed where the manipulator main body 11 is a reference posture (neutral posture) as a reference. These directions are for convenience of explanation, and the manipulator main body 11 can be used in any orientation (for example, the up and down may be inverted).

The manipulator main body 11 includes an operating unit 14 that is gripped and operated by hands and a working unit 16 that can be attached to and detached from the operating unit 14. The operating unit 14 configures a portion of the above-disclosed body 21 and includes a pair of upper covers 25a and 25b that configures a housing and extends in an approximately L shape in the Z1 direction and the Y2 direction, a drive unit 30 that is accommodated in the upper covers 25a and 25b, and a composite input unit 24 (second input unit) that is operated by hands.

The drive unit 30 includes a first motor (first actuator) 50a and a second motor (second actuator) 50b that is a drive source 50 for changing the posture of the tip operating unit 12, a driving force of the drive source 50 is mechanically transmitted to the tip operating unit 12, and therefore, the drive unit is configured so that the posture of the tip operating unit 12 is changed. A master switch 34 is provided so as to be exposed from the upper covers 25a and 25b in the vicinity of the top in the Y1 direction of the operating unit 14, and a LED 35 is provided at a place at which the master switch 34 is observed relatively easily in the Z1 direction.

A portion that extends in the Y2 direction at the base end side of the operating unit 14 is configured by a grip handle 26 that is gripped by hands. The composite input unit 24 is provided on an inclined surface of the upper portion of the grip handle 26, a rotation operation and a tilting operation in the left and right directions are performed individually or in combination, signals according to the operation are sent to the controller 29, the controller 29 controls the drive of the drive unit 30, and therefore, the posture change of the tip operating unit 12 is performed.

The working unit 16 includes a pair of lower covers 37a and 37b that is approximately symmetrically divided in the Z direction as a housing, and includes the tip operating unit 12, a shaft 18 that is provided at the tip of the tip operating unit 12 and is long and hollow, a pulley box 32 to which the base end side of the shaft 18 is fixed and is accommodated in the lower covers 37a and 37b, and a trigger lever (first input unit) 36 that is rotatably pivoted about the center in the X direction with a trigger shaft 39 as a supporting point. The lower covers 37a and 37b, the pulley box 32, and the trigger lever 36 configure a portion of the above-disclosed body 21.

The tip operating unit 12 includes an end effector 300 that is opened and closed based on the operation of the trigger lever 36 and a posture change mechanism 13 that changes the posture of the end effector 300 based on the operation of the composite input unit 24. For example, the end effector 300 is a gripper that grips a portion of a living body or a needle for suture, or scissors that cut a portion of a living body, and is configured so as to open and close based on a predetermined opening and closing shaft. The opening and closing operations of the end effector 300 are performed so as to be mechanically transmitted based on the operation (press-pull operation) of the trigger lever 36 by hands.

The trigger lever 36 includes an arm portion 36a that is pivotally supported to a trigger shaft 39 provided in the end in the Z2 direction side in the inner portion of the lower covers 37a and 37b and a trigger operator 36b that is provided at the Y2 side of the arm portion 36a. The trigger operator 36b includes a ring portion 36c and an approximately arc shaped finger engageable protrusion 36d that is provided at the Y2 side of the ring portion 36c.

The posture change mechanism 13 can perform a roll operation of rotation based on a roll axis (Z axis at the time of neutral posture) oriented toward the tip and a yaw operation (tilting operation) of tilting based on a yaw axis in the Y direction, and can perform the roll operation and the tilting operation selectively or in combination. Accordingly, the tip operation unit 12 can perform a three-axis operation that includes the opening and closing operations, the roll operation, and the yaw operation of the end effector 300. For example, the drive source 50 is driven based on the operation of the composite input unit 24, and wherein the driving force of the drive source 50 is mechanically transmitted to the tip operating unit 12, and therefore, the operation of the posture change of the end effector 300 (roll operation and yaw operation) is performed.

In addition, the mechanical transmission transmits a force via a wire, a chain, a timing belt, a link, a rod, and a gear, and is mainly driven via mechanical components, which are made of a non-elastic solid, in a power transmission direction. Some inevitable extension may be generated due to the tension in the wire, and the chain, however, these are regarded as mechanical components made of a non-elastic solid.

The working unit 16 is connected and fixed to the operating unit 14 by a pair of left and right detachable levers 40 and 40 that is provided in the operating unit 14 and can be detached from the operating unit 14 through the opening operation of the detachable lever 40, and therefore, replacement work can be performed relatively easily in a surgery site without using a special instrument.

The tip operating unit 12 and the shafts 18 are configured with a small diameter, can be inserted into a body cavity 22 through a cylindrical trocar 20 mounted on an abdomen of a patient, and can perform various kinds of manipulation such as affected part excision in the body cavity 22, gripping, suture, or ligation, through operations of the composite input unit 24 and the trigger lever 36.

The controller 29 is a control portion that collectively controls the manipulator main body 11 and is connected to a cable 28 that extends from the lower end of the grip handle 26. For example, a portion or all of functions of the controller 29 can be integrally mounted in the operating unit 14. For example, the controller 29 includes a first port 27a, a second port 27b, and a third port 27c, and can independently and simultaneously control three manipulator main bodies 11.

The controller 29 can be connected to a host computer 31 which is use history management means via communication means such as a LAN. The host computer 31 records a use history table at recording means (not shown) of the inner portion, sends and receives use history data according to an individual identification number (identification number) to the controller 29 or a plurality of controllers 29 connected through the LAN, and manages the use history data. The host computer 31 is not limited to a configuration independent of the controller 29 and the functions of the host computer may be provided in the inner portion of the controller 29.

Figure 2:
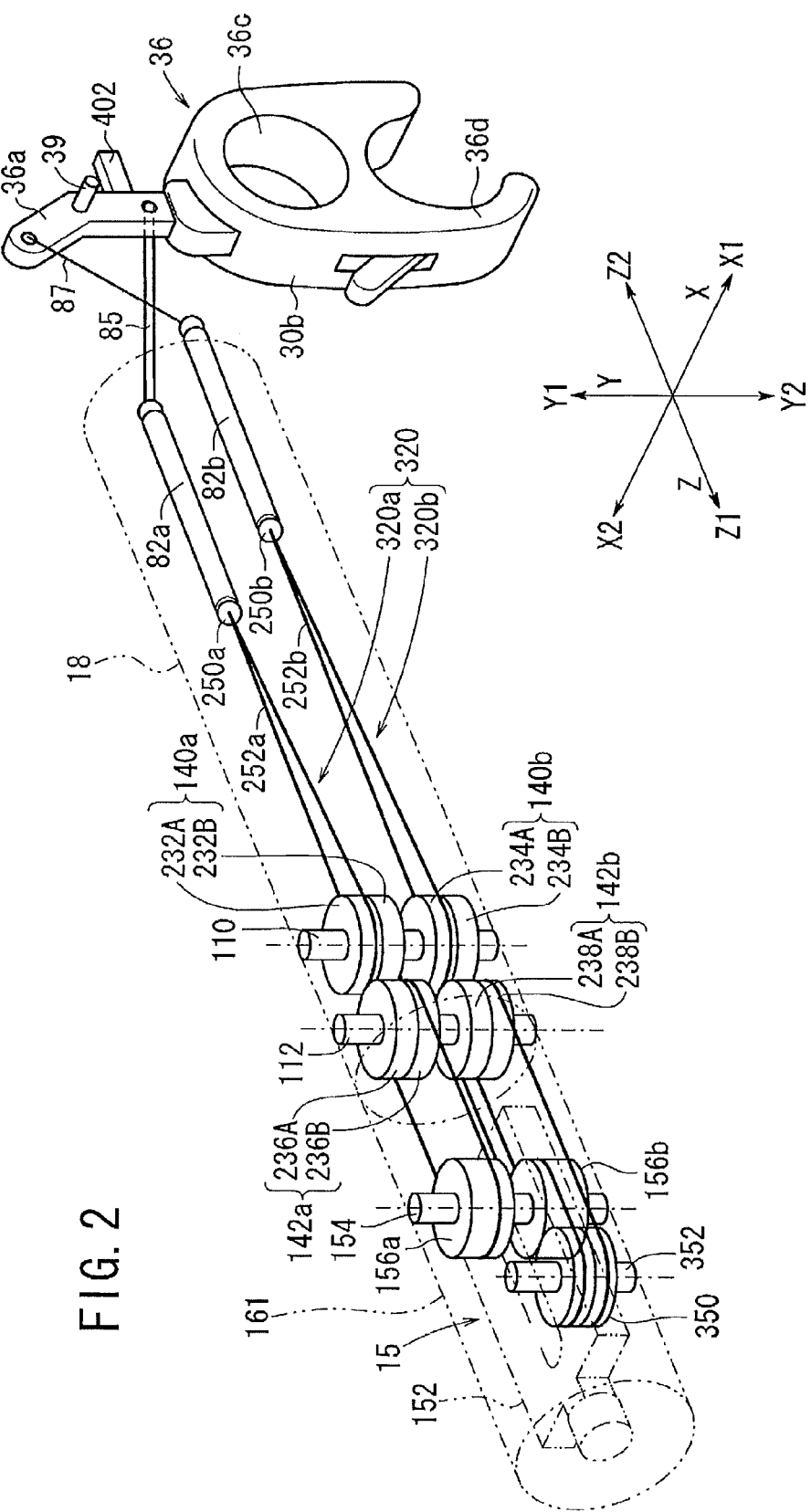
FIG. 2 is a schematic view of an end effector drive mechanism when the trigger lever is pushed out.
Figure 3:
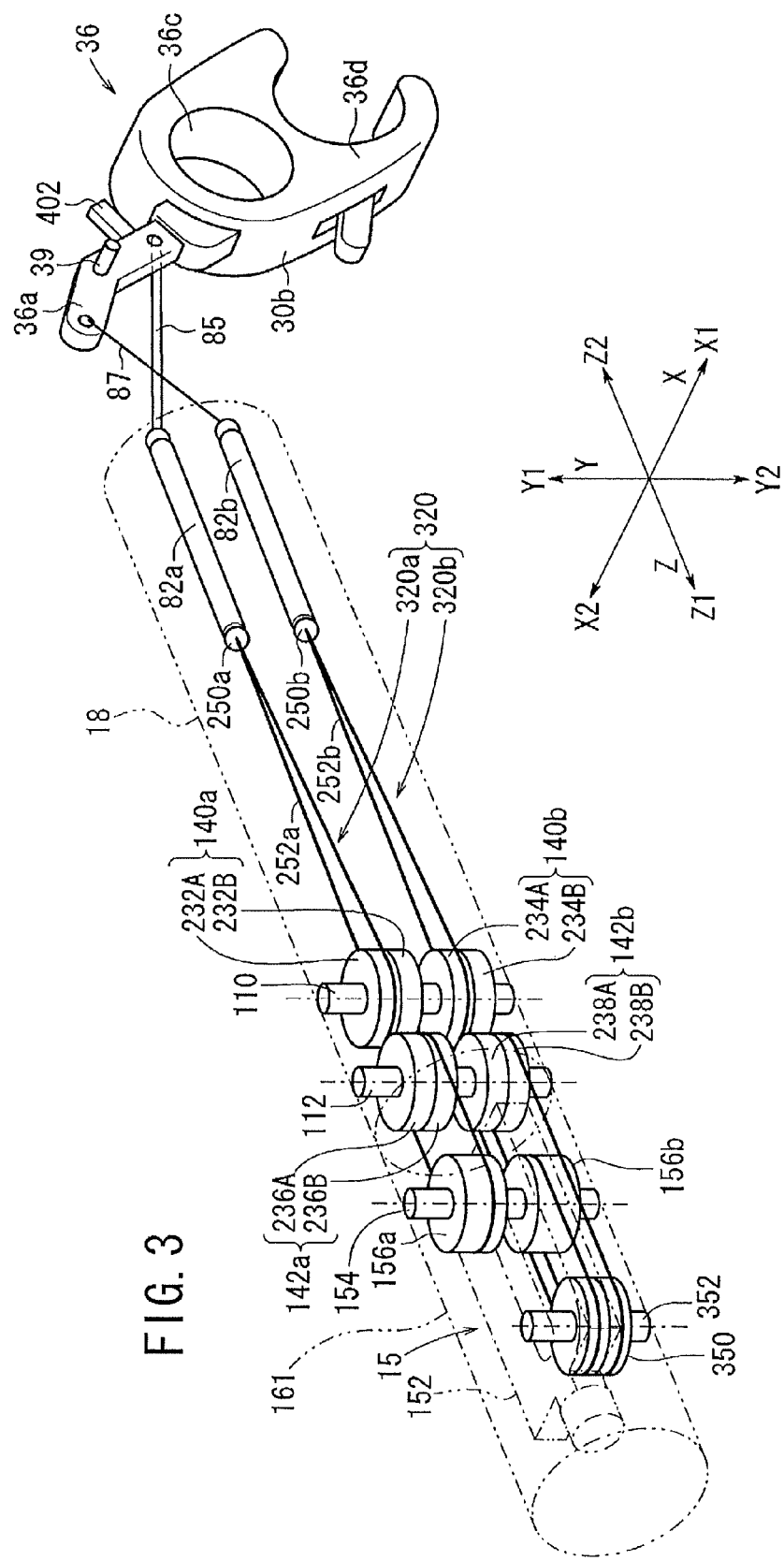
FIG. 3 is a schematic view of the end effector drive mechanism when the trigger lever is sufficiently pulled.
Figure 4:
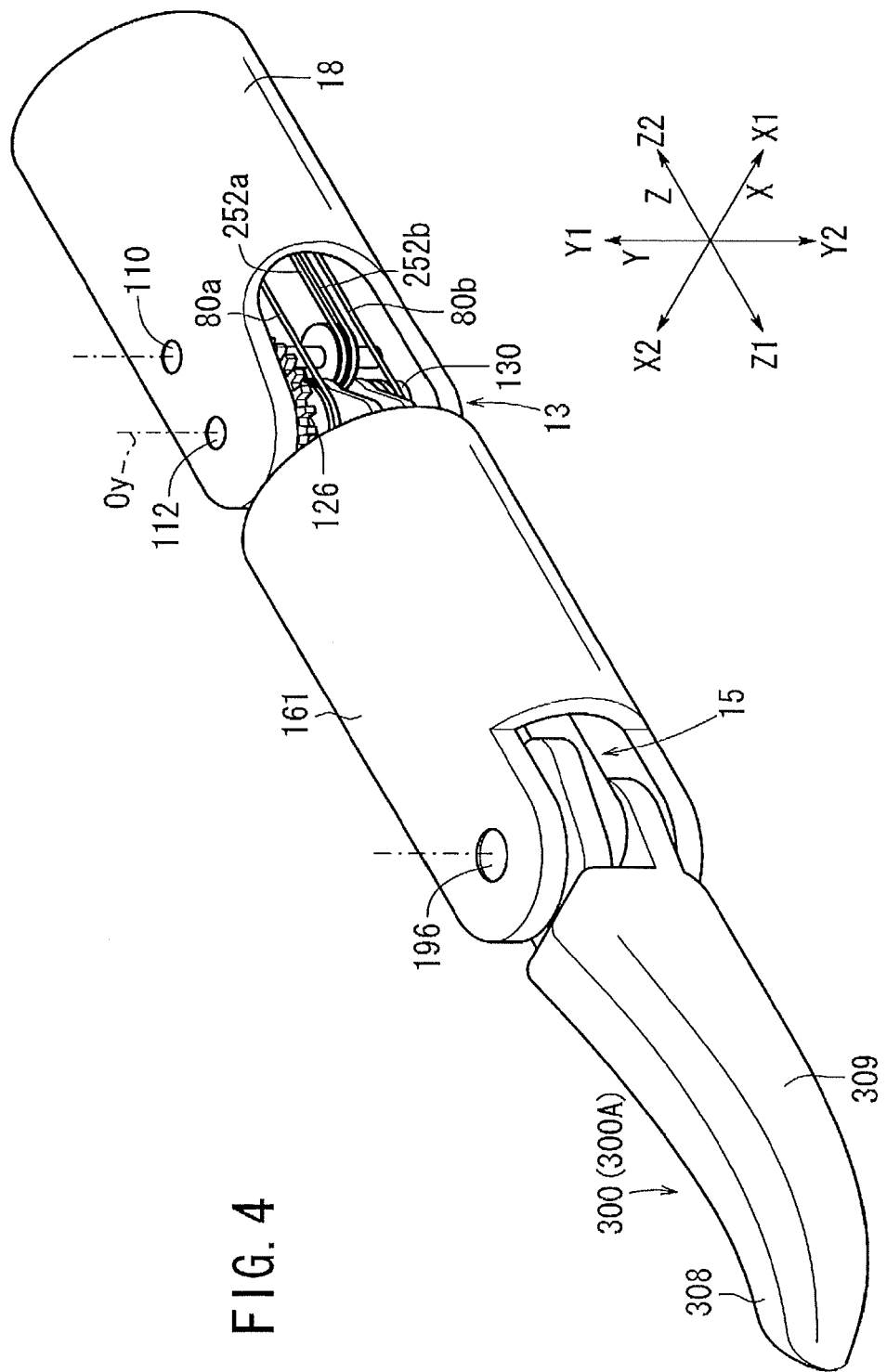
FIG. 4 is a perspective view of a tip operating unit.
Figure 5:
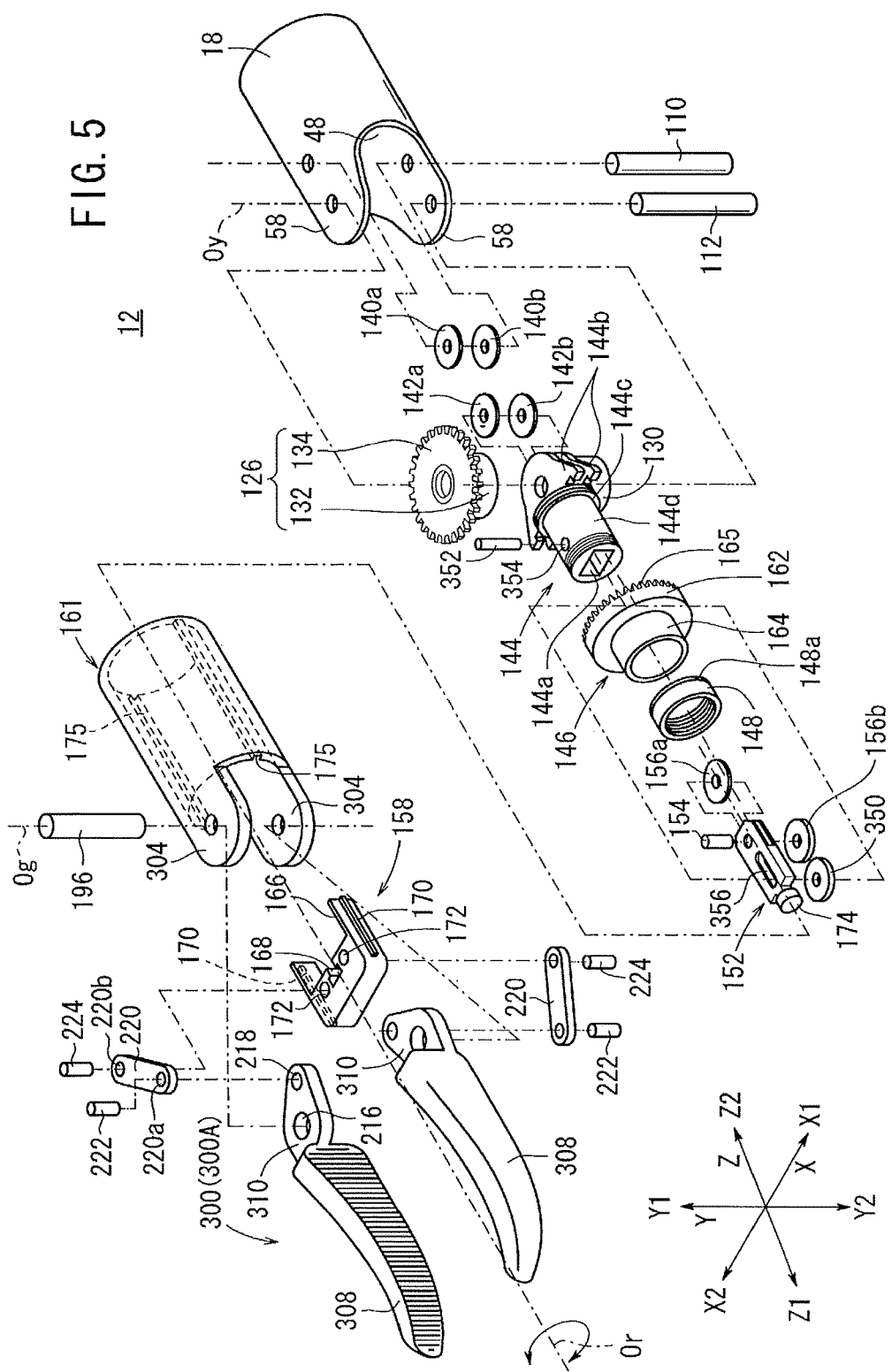
FIG. 5 is an exploded perspective view of the tip operating unit.

Next, with reference mainly to FIGS. 2 and 3 and with reference to FIGS. 4 and 5, an end effector drive mechanism 320 that is operated based on the operation (press-pull operation) of the trigger lever 36 will be disclosed.

The operation of the end effector drive mechanism 320 is converted into the operation (opening and closing operations) of the end effector 300 by a conversion mechanism 15. The conversion mechanism 15 includes a transmitting member 152 that can advance and retreat in the extension direction of the end effector 300, and if the transmitting member 152 moves to the advance position which is the Z1 direction side shown in FIG. 2, the end effector 300 becomes an opened state (refer to FIG. 7), and if the transmitting member 152 moves to the retreat position which is the Z2 direction side shown in FIG. 3, the end effector 300 becomes a closed state (refer to FIG. 8). According to the advance and retreat operations of the transmitting member 152, the end effector 300 is opened and closed. In addition, the conversion mechanism 15 includes components other than the transmitting member 152.

The end effector drive mechanism 320 includes a first mechanism 320a that moves the transmitting member 152 to the retreat position when the trigger lever 36 is pulled in the Z2 direction, and a second mechanism 320b that moves the transmitting member 152 to the advance position when the trigger lever 36 is pressed in the Z1 direction. In the descriptions below, a is added to reference numerals of the components of the first mechanism 320a, b is added to reference numerals of the components of the second mechanism 320b, and both are distinguished from each other. With respect to components having similar functions in the components in the first mechanism 320a and the components in the second mechanism 320b, in order to avoid complication, only the components in the first mechanism 320a may be representatively disclosed.

The first mechanism 302a includes a connection rod 85 that is connected to the base end side (trigger operator 36b side) of the arm portion 36a of the trigger lever 36 rather than the trigger shaft 39 of the arm portion 36a of the trigger lever 36, a rod 82a that is connected to the Z1 side of the connection rod 85, an idle pulley 140a that is disposed so as to be separated from the Z1 side of the rod 82a, a guide pulley 142a that is disposed so as to be separated from the Z1 side of the idle pulley 140a, a driven pulley 156a that is disposed at the end effector 300 side rather than the guide pulley 142a, and a driven wire 252a that is wound around the idle pulley 140a, the guide pulley 142a, and the driven pulley 156a.

Two shafts 110 and 112 that are separated from each other in the Z direction and cross in a radial direction in the inner portion of the shaft 18 are disposed so as to be parallel to each other in the tip of the shaft 18, the idle pulley 140a is rotatably pivoted at the shaft 110, and the guide pulley 142a is rotatably pivoted at the shaft 112. The idle pulley 140a is configured so that a first layer idle pulley 232A and a second layer idle pulley 232B that can be rotated to be independent from each other are disposed at the same axis as each other. The guide pulley 142a is configured so that a first layer guide pulley 236A and a second layer guide pulley 236B that can be rotated to be independent from each other are disposed at the same axis as each other.

A pin 154 parallel to the shaft 112 is inserted into the transmitting member 152, and the driven pulley 156a is rotatably pivoted with respect to the pin 154. The driven pulley 156a and the transmitting member 152 can simultaneously move in the extension direction of the end effector 300 (Z direction when the end effector 300 is a neutral posture). A portion of the rod 82a and the driven wire 252a is inserted into the inner portion of the shaft 18. For example, the rod 82a is a stainless steel pipe or a solid rod that is sufficiently strong and thin, and a portion of the rod 82a that is close in the Z1 direction is positioned in the inner portion of the shaft 18.

A portion of the driven wire 252a is an annular (endless shaped) flexible member that is engaged to a wire engagement portion 250a provided at the end of the Z1 side of the rod 82a. The driven wire 252a may be a rope, a resin wire, a piano wire, or a chain. The annulus has a wide sense, and the flexible member does not necessarily need to be applied over the entire length of the driven wire. For example, if at least a portion of the driven wire which is wound around each pulley is the flexible member, and a straight line portion of the driven wire may be connected by a rigid body.

The driven wire 252a is disposed from the rod 82a toward the X2 direction (second side) through the X1 direction (first side) of the first layer idle pulley 232A, and reaches the surface in the X2 direction of the driven pulley 156a through the surface in the X2 direction of the first layer guide pulley 236A. In addition, the driven wire 252a is disposed in a path in which the driven wire is wound around a semicircle of the surface in the Z1 direction of the driven pulley 156a, reaches the surface in the X1 direction, through the surface in the X1 direction of the second layer guide pulley 236B, and reaches the wire engagement portion 250a through the X2 direction of the second layer idle pulley 232B toward the X2 direction.

The idle pulley 140a, the guide pulley 142a, and the driven pulley 156a have approximately the same diameter to one another, and the diameter is appropriately large within a possible range in the layout so that the driven wire 252a is not bent too much. The wire engagement portion 250a is provided at a position which is appropriately separated from the idle pulley 140a so that the driven wire 252a is not excessively bent, and both ends of the driven wire 252a form an acute angle with the wire engagement portion 250a as an apex. A gap between the idle pulley 140a and the guide pulley 142a is narrow, and for example, a gap approximately the same as the width of the driven wire 252a is formed. In order to help prevent the slip-off of the driven wire 252a, small flanges may be provided on the upper surfaces and lower surfaces of the idle pulley 140a, the guide pulley 142a, and the driven pulley 156a, and the side surfaces may be formed in a concave shape.

In the first mechanism 320a that is configured as disclosed above, if the trigger lever 36 is pulled, the arm portion 36a is rotated about the trigger shaft 39 in a counterclockwise direction in FIG. 3, and therefore, the rod 82a moves in the Z2 direction through the connection rod 85. The driven wire 252a connected to the rod 82a moves in the Z2 direction, and the driven pulley 156a moves toward the retreat position (right direction in FIG. 3) according to the movement in the Z2 direction of the driven wire 252a. At this time, the transmitting member 152 moves along with the driven pulley 156a.

In addition, according to the movement in the Z2 direction of the driven wire 252a, the first layer idle pulley 232A and the second layer idle pulley 232B rotate in directions opposite to each other, and the first layer guide pulley 236A and the second layer guide pulley 236B rotate in directions opposite to each other. The idle pulley 140a and the guide pulley 142a are configured so that two pulleys having the same axis as each other respectively are disposed in parallel, and therefore, the pulleys can rotate in a reverse direction according to the movement of the driven wire 252a that abuts the pulley, and the operation is relatively smoothly performed.

As shown in FIGS. 2 and 3, the second mechanism 320b includes a configuration in which a return pulley 350 is substantially added to the first mechanism 320a. The driven pulley 156a and the driven pulley 156b include a configuration having the same axis as each other. The second mechanism 320b includes a wire 87 that is connected further toward a tip side (side opposite to the ring portion 36c based on the trigger shaft 39) than the trigger shaft 39 of the arm portion 36a of the trigger lever 36, a rod 82b that is connected to the Z1 side of the wire 87, an idle pulley 140b that is disposed so as to be separated from the Z1 side of the rod 82b, a guide pulley 142b that is disposed so as to be separated from the Z1 side of the idle pulley 140b, a driven pulley 156b that is disposed at the end effector 300 side rather than the guide pulley 142b, a return pulley 350 that is disposed so as to be separated from the end effector 300 side rather than the driven pulley 156b, and a driven wire 252b that is wound around the idle pulley 140b, the guide pulley 142b, the driven pulley 156b, and the return pulley 350.

The idle pulley 140b is rotatably pivoted at the shaft 110. The idle pulley 140b is configured so that a first layer idle pulley 234A and a second layer idle pulley 234B that can be rotated to be independent from each other are disposed at the same axis as each other. The guide pulley 142b is rotatably pivoted at the shaft 112. The guide pulley 142b is configured so that a first layer guide pulley 238A and a second layer guide pulley 238B that can be rotated to be independent from each other are disposed at the same axis as each other.

The driven pulley 156b is rotatably pivoted so as to be independent from and have the same mutual axis as the driven pulley 156a due to the pin 154 in a hole 144a (refer to FIG. 5) provided in a main shaft member 144 disclosed below. The two driven pulleys 156a and 156b and the transmitting member 152 can simultaneously move in the extension direction of the end effector 300. The driven pulley 156b has a width in which the driven wire 252b can be wound twice.

The return pulley 350 is rotatably pivoted by a pin 352 that is disposed in the inner portion of a hollow cylindrical tip cover 161 (refer to FIGS. 4 and 5), and the position of the return pulley can be fixed at the inner portion of the tip cover 161. The return pulley 350 has a width in which the driven wire 252b can be wound twice. In addition, the return pulley 350 is formed in two layers, the two layered pulleys can be rotated in directions opposite to each other at the time of the opening and closing operations, and therefore, friction between the driven wire 252b and the return pulley can be decreased.

A portion of the rod 82b and the driven wire 252b is inserted into the inner portion of the shaft 18. A portion of the driven wire 252b is an annular flexible member that is engaged to a wire engagement portion 250b provided at the end of the Z1 side of the rod.

The driven wire 252b is disposed from the wire engagement portion 250b of the rod 82b toward the X2 direction through the X1 direction of the first layer idle pulley 234A, and reaches the surface in the X2 direction of the driven pulley 156b through the X2 direction of the first layer guide pulley 238A. The driven wire 252b extends toward the Z1 direction as it is, reaches the surface in the X2 direction of the return pulley 350, is wound a half turn around the surface in the Z1 direction of the return pulley 350, and returns in the Z2 direction.

In addition, the driven wire 252b is wound a half turn around the surface in the Z2 direction of the driven pulley 156b, reaches the return pulley 350 again through the X2 side, is wound a half turn around the surface in the Z1 direction of the return pulley 350 again, and returns in the Z2 direction. Thereafter, the driven wire 252b reaches in the X2 direction of the second layer idle pulley 234B from the X1 direction of the second layer guide pulley 238B, and reaches the wire engagement portion 250b of the rod 82b.

In the second mechanism 320b that is configured as disclosed above, if the trigger lever 36 is pushed out, the arm portion 36a is rotated about the trigger shaft 39 in a clockwise direction in FIG. 2, and the rod 82b moves in the Z2 direction via the wire 87. The driven wire 252b connected to the rod 82b is drawn out in the Z2 direction at the place of the wire engagement portion 250b and moves. Since the driven wire 252b is wound around the driven wire 252b via the return pulley 350, the driven pulley 156b moves in the left direction in FIG. 2. At this time, the transmitting member 152 also moves along with the driven pulley 156b. In addition, according to the movement of the driven wire 252b, the first layer idle pulley 234A and the second layer idle pulley 234B rotate in directions opposite to each other, and the first layer guide pulley 238A and the second layer guide pulley 238B rotate in directions opposite to each other.

According to the end effector drive mechanism 320, the press-pull operation of the trigger lever 36 is converted to the advance and retreat operation of the transmitting member 152. As disclosed above, the transmitting member 152 performs the advance and retreat operation, and therefore, the opening and closing operations of the end effector 300 are performed.

With reference to FIGS. 4 to 8, the conversion mechanism 15 that converts the operation of the above-disclosed end effector drive mechanism 320 to the operation (opening and closing operations) of the end effector 300 will be disclosed. The end effector 300 that performs the opening and closing operations through the conversion mechanism 15 is configured as a gripper 300A in the illustrated example. The gripper 300A includes a pair of gripper members 308 and is configured as an opening and closing mechanism that can be opened and closed. Lever portions 310 are provided on the base end sides of each of the gripper members 308. Shaft holes 216 are formed in each of the lever portions 310.

A hollow cylindrical tip cover 161 is disposed in the Z1 direction side of the shaft 18 as a whole, and a pair of protrusion pieces 304 is provided at the tip of tip cover 161. The lever portions 310 of the pair of gripper members 308 are disposed so as to be overlapped with each other between the pair of protrusion pieces 304. A pin 196 that is fixed between the pair of protrusion pieces 304 of the tip cover 161 is inserted into the shaft holes 216 of the lever portions 310, and each of the lever portions 310 is rotatably pivoted to the tip cover 161 with an opening and closing axis Og as a center. Thereby, the opening and closing operations of the gripper 300A can be performed. The movable ranges of the gripper members 308 with the opening and closing axis Og as the center may be set so that the gripper 300A is opened to 40° or equal to or more than 40°, for example.

The conversion member 15 includes a pair of link members 220 that is connected to the lever portions 310 of the pair of gripper members 308 via pins 222, a passive plate 158 that is connected to the link members 220 via pins 224, and the above-disclosed transmitting member 152 that is engaged to be relatively rotated with respect to the passive plate 158.

Pin holes 218 are formed in the base end of the lever portions 310, pin holes 220a are formed in one set of ends of the link members 220, and the pin 222 is inserted into the pin holes 218 and 220a. The link members 220 are rotatably connected to the lever portions 310 of the gripper members 308 via the pin 222.

Pin holes 220b are formed in the other ends of the link members 220, and the pin 224 is inserted into the pin holes 220b. The link members 220 are rotatably connected to a passive plate 158 via the pin 224. Each of the link members 220 is disposed so as to be inclined to the axial line of the tip cover 161 so that one link member 220 crosses the other link members 220 in the intermediate portion in a plan view.

As shown in FIG. 5, the passive plate 158 includes a concave portion 166 in the Z2 direction, an engagement portion 168 that is provided on the bottom surface of the concave portion 166, ribs 170 in the axial direction that are each provided at both end surfaces in the X direction, and two link holes 172. The engagement portion 168 has a shape that engages with a mushroom shaped protrusion 174 provided at the tip of the transmitting member 152. According to the engagement, the passive plate 158 and the transmitting member 152 can perform the rotation of the relative roll axis.

The ribs 170 of the passive plate 158 are fitted to two grooves 175 that are formed on the inner surface of the tip cover 161, and therefore, the passive plate 158 is guided in the axial line direction (roll axis Or direction) of the tip cover 161. Since the protrusion 174 that is provided at the tip of the transmitting member 152 engages with the engagement portion 168 of the passive plate 158, the passive plate 158 and the transmitting member 152 can simultaneously move in the axial direction of the tip cover 161 in the inner portion of the tip cover 161.

Figure 7:
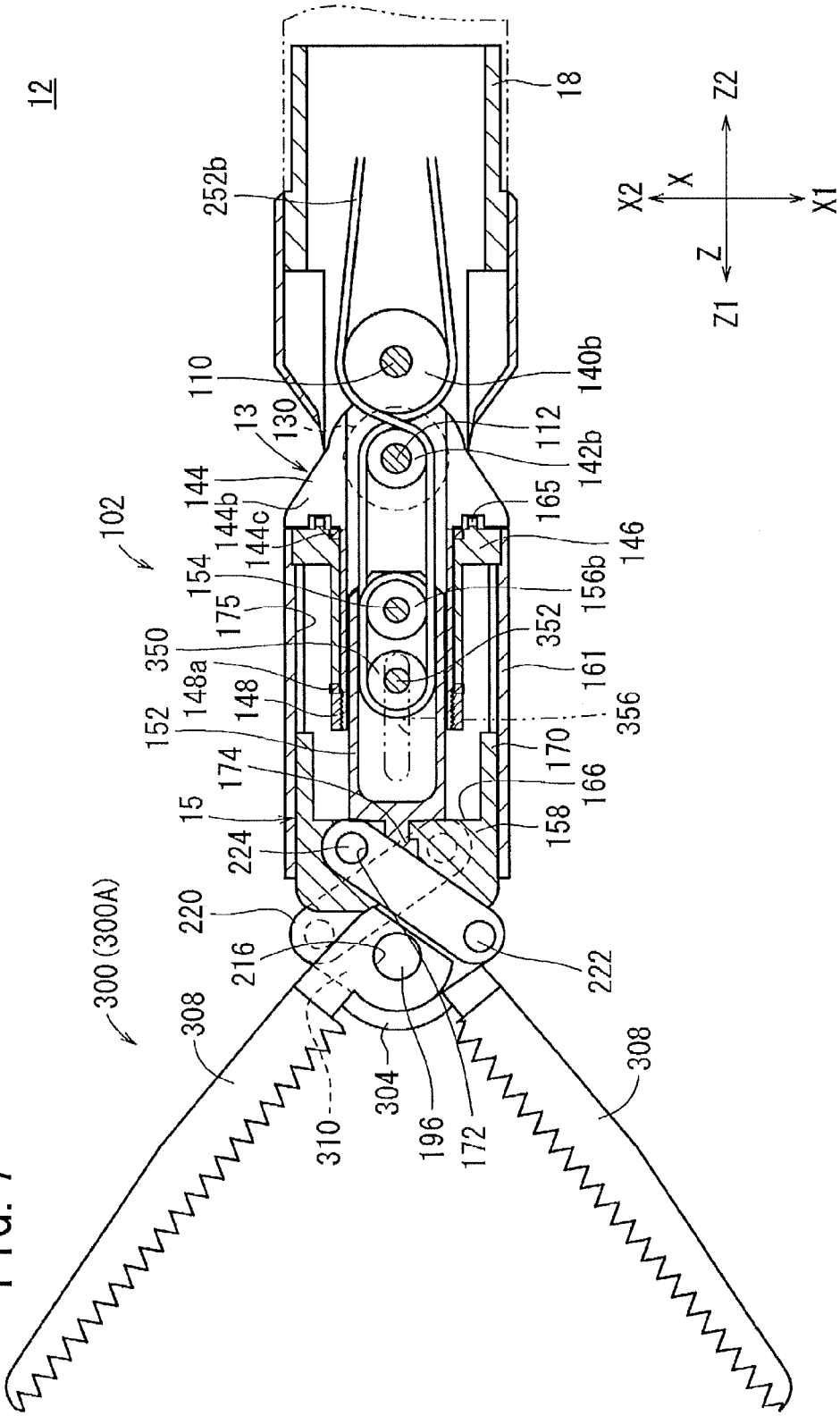
FIG. 7 is a cross-sectional plan view of the tip operating unit in a state where a gripper is opened.
Figure 8:
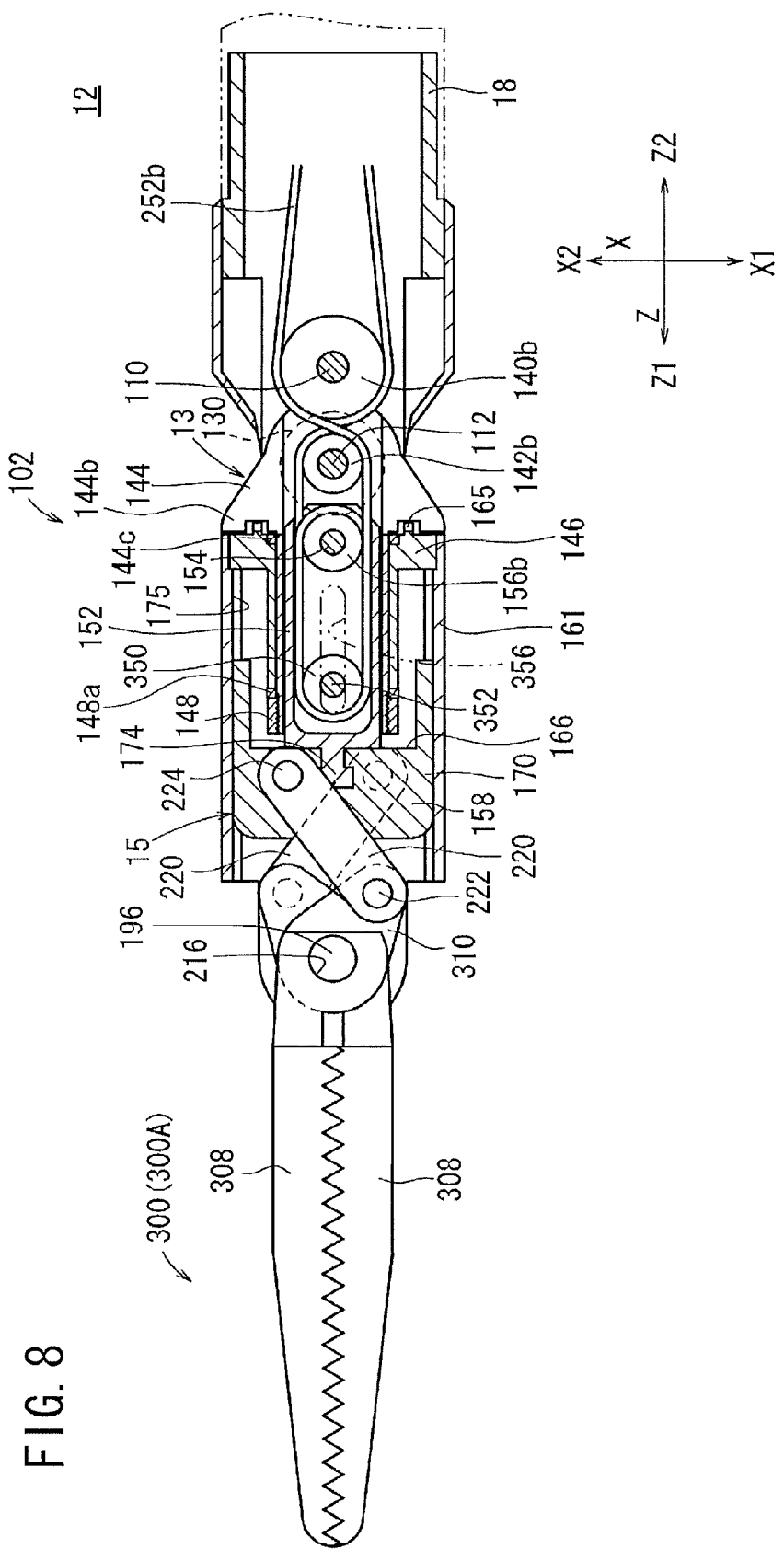
FIG. 8 is a cross-sectional plan view of the tip operating unit in a state where the gripper is closed.

As disclosed above, if the transmitting member 152 moves in the advance direction (left direction in FIG. 7) according to the push operation of the trigger lever 36, the passive plate 158 moves in the same direction, the link acts on the lever portions 310 according to the movement of the passive plate 158, and therefore, the gripper 300A is opened as shown in FIG. 7. If the transmitting member 152 moves in the retreat direction (right direction in FIG. 8) according to the pull operation of the trigger lever 36, the passive plate 158 moves in the same direction, the link members 220 acts on the lever portions 310 according to the movement of the passive plate 158, and therefore, the gripper 300A is closed as shown in FIG. 8.

Since the force that pushes out the trigger lever 36 by hands is directly transmitted by the above-disclosed second mechanism 320b (refer to FIG. 3) to the gripper 300A in a mechanical manner, the gripper can be opened not by a predetermined force such as an elastic body but by an arbitrary strong force. Therefore, living body tissues are separated using the outer side surfaces of the gripper 300A, or the gripper can be appropriately used with respect to manipulation such as expansive opening of a hole portion. In addition, when an object contacts the outer side surfaces of the gripper 300A, the driven wire 252b, the rod 82b, and the trigger lever 36 also cannot further move in the Z1 direction, an operator can perceive contacting of the outside surfaces of the gripper 300A to the object, and hardness of the object through the fingertips.

Figure 6:
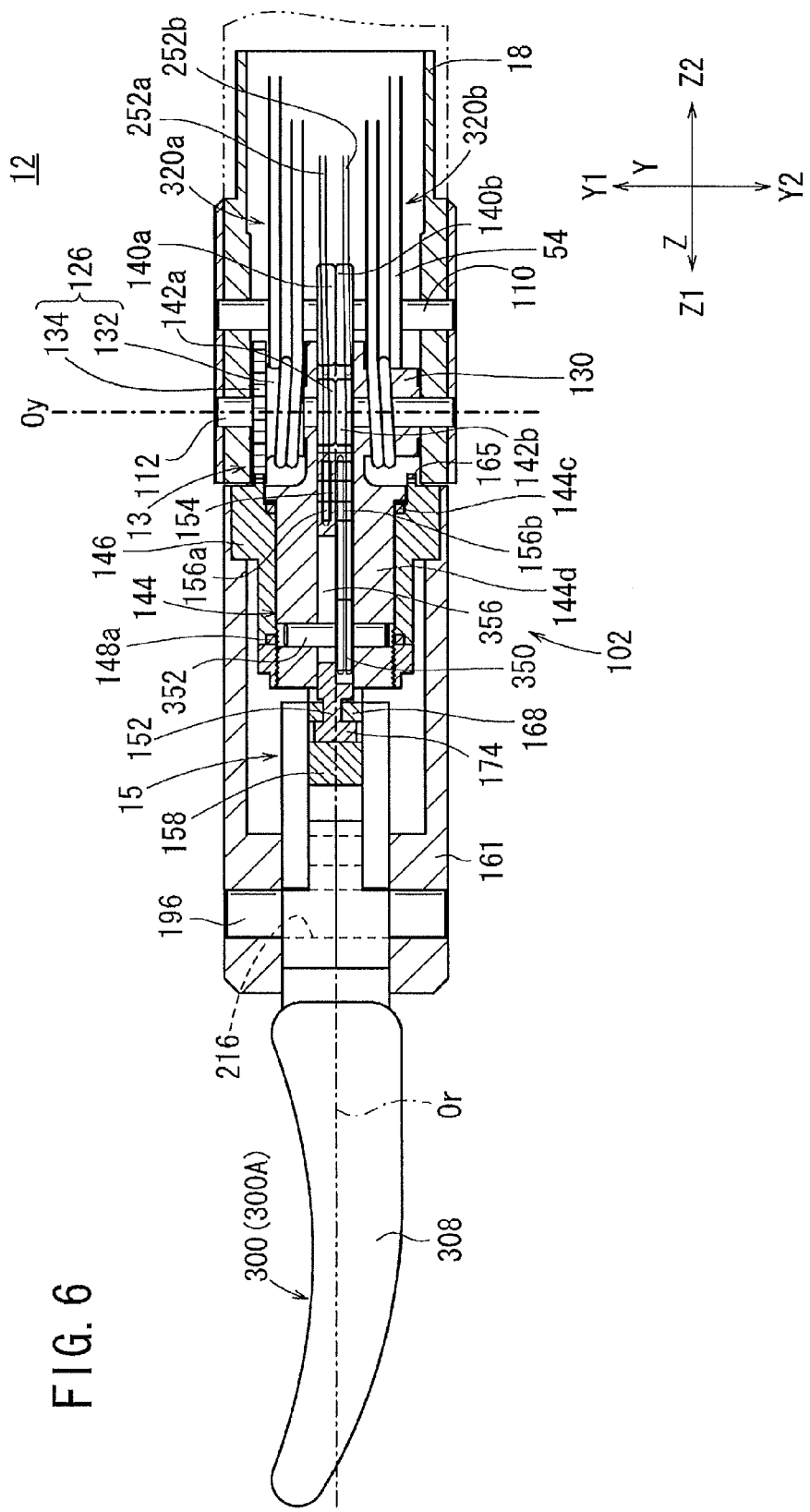
FIG. 6 is a cross-sectional side view of the tip operating unit.

As shown in FIG. 6, the protrusion 174 that is provided at the tip of the transmitting member 152 engages with the engagement portion 168 of the passive plate 158 so as to be rotated with the roll axis Or as a center. As disclosed below, the tip cover 161 can rotate to a main shaft member 144 that is pivotally supported so as to be tiltable to the tip of the shaft 18 with the roll axis as a center. Accordingly, the gripper 300A, the link members 220, the passive plate 158, and the tip cover 161 can rotate along with the roll axis Or as a center.

Figure 9:
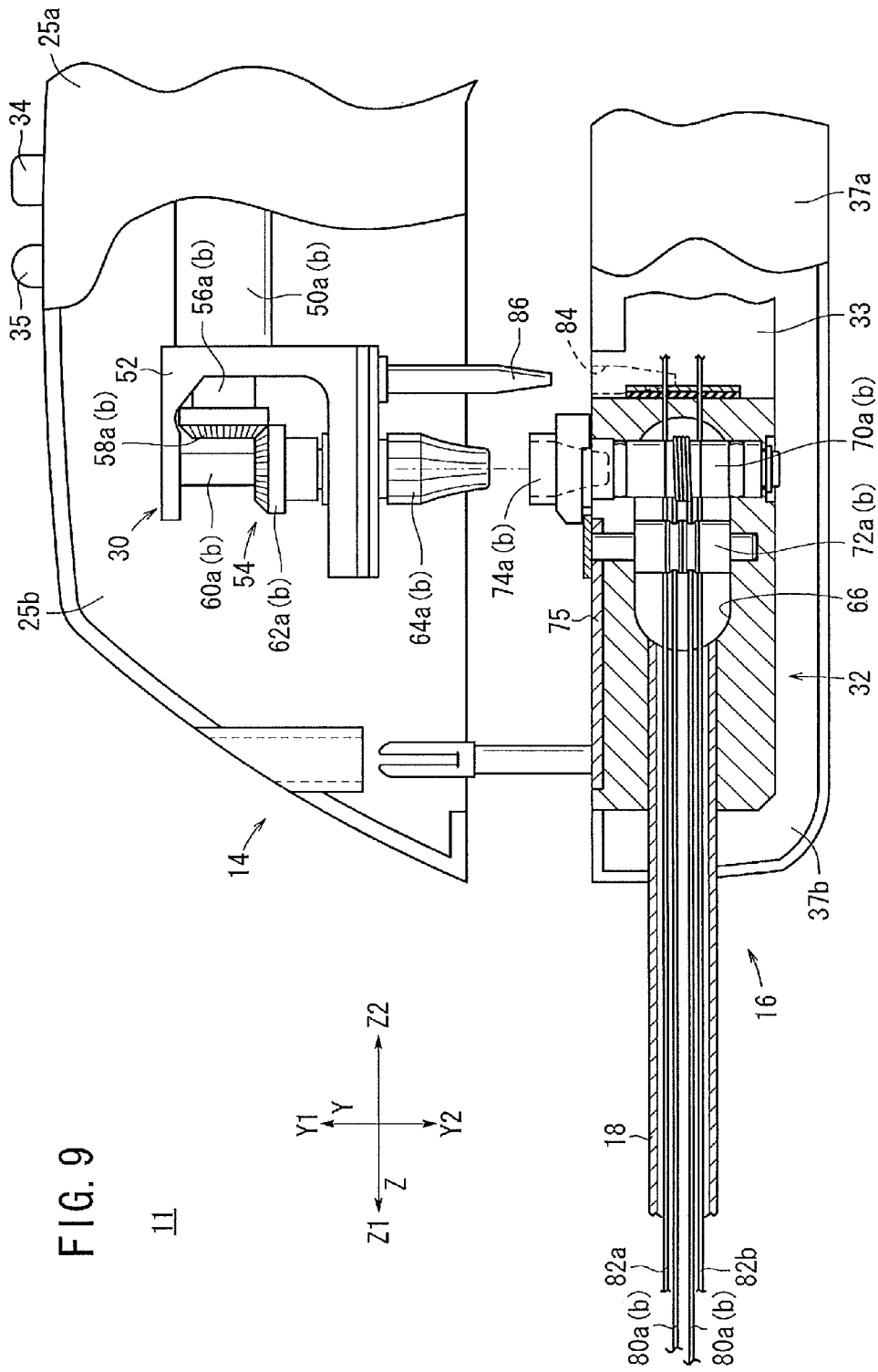
FIG. 9 is a partial cross-sectional side view of the medical manipulator in a state where a working unit and an operating unit are separated from each other.
Figure 10:
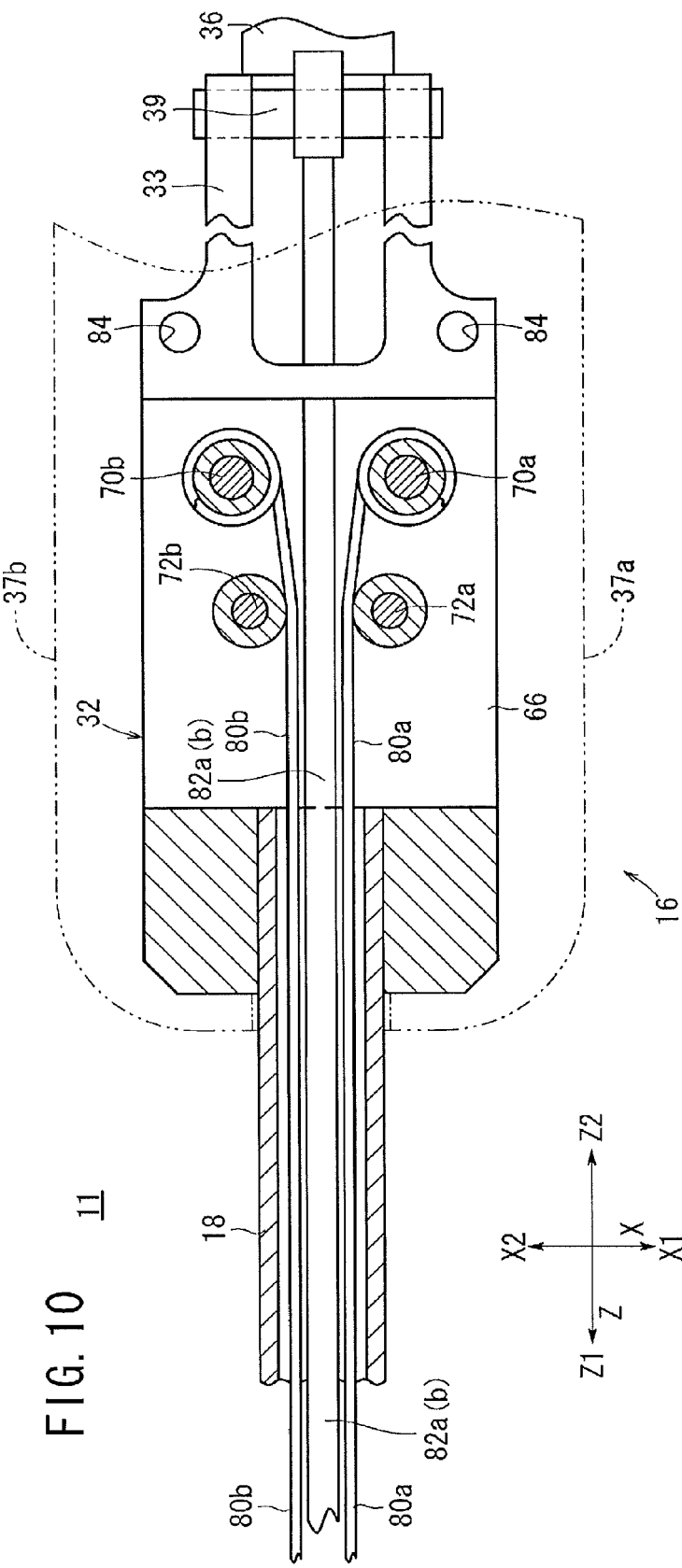
FIG. 10 is a cross-sectional plan view in which a portion of the working unit is omitted.

A mechanism that mechanically transmits the driving force of the drive unit 30 to the tip operating unit 12 will be disclosed. FIG. 9 is a partial cross-sectional side view of the manipulator main body 11 in a state where the working unit 16 and the operating unit 14 are separated from each other. FIG. 10 is a cross-sectional plan view in which a portion of the working unit 16 is omitted. Two rods 82a and 82b that are components of the above-disclosed end effector drive mechanism 320 penetrate in the Z direction so as to be lined up in the Y direction in a cavity portion 66 that configures the pulley box 32.

As shown in FIGS. 9 and 10, a pair of pinholes 84 and 84 that is symmetrical based on the Z direction is formed at the Z2 side of the pulley box 32. A pair of guide pins 86 and 86 that protrudes in the Y1 direction from the bottom surface of the bracket 52 is inserted into each of the pinholes 84 and 84 at the time of the mounting of the working unit 16 and the operating unit 14, and therefore, the operating unit 14 and the working unit 16 are positioned and mounted so as to have high stiffness.

The drive unit 30 includes the above-disclosed first and second motors 50a and 50b, a bracket 52 that supports the first and second motors 50a and 50b, and a gear mechanism portion 54 that converts the rotation directions of the first and second motors 50a and 50b and transmits the driving force to the working unit 16 side. The first and second motors 50a and 50b have a columnar form, output shafts 56a and 56b that are decelerated by a reduction gear (not shown) penetrate one surface of the bracket 52, and driving bevel gears 58a and 58b configuring the gear mechanism portion 54 are fixed to the output shafts 56a and 56b. For example, the first and second motors 50a and 50b are DC motors, and a rotary encoder is provided as an angle sensor (not shown).

The gear mechanism portion 54 is provided in a space within the bracket 52, and includes two drive shafts 60a and 60b that are lined up in the X direction and two driven bevel gears 62a and 62b that are fixed to each of the drive shafts 60a and 60b and engaged with the driving bevel gears 58a and 58b. The output shafts 56a and 56b of the first and second motors 50a and 50b, and the drive shafts 60a and 60b, are pivotally supported to the bracket 52 through bearings (not shown). The lower end side of the drive shaft 60a (60b) protrudes from the lower surface of the bracket 52, and for example, an engaging protrusion 64a (64b) that has a cross-section of a hexagonal waveform and a taper shape with a tapered tip is provided in the tip of the protruded lower end.

The pulley box 32 includes a cavity portion 66 in which both ends are opened in the X direction, and pulleys (driven shafts) 70a and 70b and wire guide portions 72a and 72b that are accommodated in the cavity portion 66, and the shaft 18 are fixed and supported to a hole portion that penetrates the Z1 side of the cavity portion 66. The pulleys 70a and 70b have the same axis as the drive shafts 60a and 60b, and engaging recesses 74a and 74b that can engage with the engaging protrusions 64a and 64b of the drive shafts 60a and 60b side are provided at the upper end side of the pulleys. The engaging recesses 74a and 74b can engage with (fit to) the engaging protrusions 64a and 64b, and for example, include a concave portion that has a cross-section of a hexagonal waveform and a taper shape having a tapered inner portion.

Accordingly, when the operating unit 14 and the working unit 16 are mounted, the engaging protrusion 64a (64b) and the engaging recess 74a (74b) engage with each other, and therefore, the rotation driving force from the drive shaft 60a (60b) can be transmitted to the pulley 70a (70b). For example, an attachment and detachment detection sensor (not shown) that detects the attachment and detachment of the operating unit 14 and the working unit 16, a phase detection sensor (not shown) that detects a phase of the drive shaft 60a, may be provided at the operating unit 14, and the engagement structure of the engaging protrusion 64a or the engaging recess 74a may have another structure.

As shown in FIG. 10, the wire guide portions 72a and 72b are disposed at the Z1 side of the pulleys 70a and 70b, and an interval between the outer circumferential surfaces of the wire guide portions is set so as to be narrower than the interval between the outer circumferential surfaces of the pulleys 70a and 70b. Wires (a power transmitting member) 80a and 80b are wound around the pulleys 70a and 70b, are guided by wire guide portions 72a and 72b, and are inserted into the shaft 18. Such wire guide portions 72a and 72b are used, and therefore, the shaft 18 can be sufficiently thin without depending on diameters of the first and second motors 50a and 50b or an axial distance between the pulleys 70a and 70b, and for example, the shaft can be set relatively easily to an outer diameter of approximately 5 mm to 10 mm that is suitable to be inserted into the trocar 20.

Figure 11:
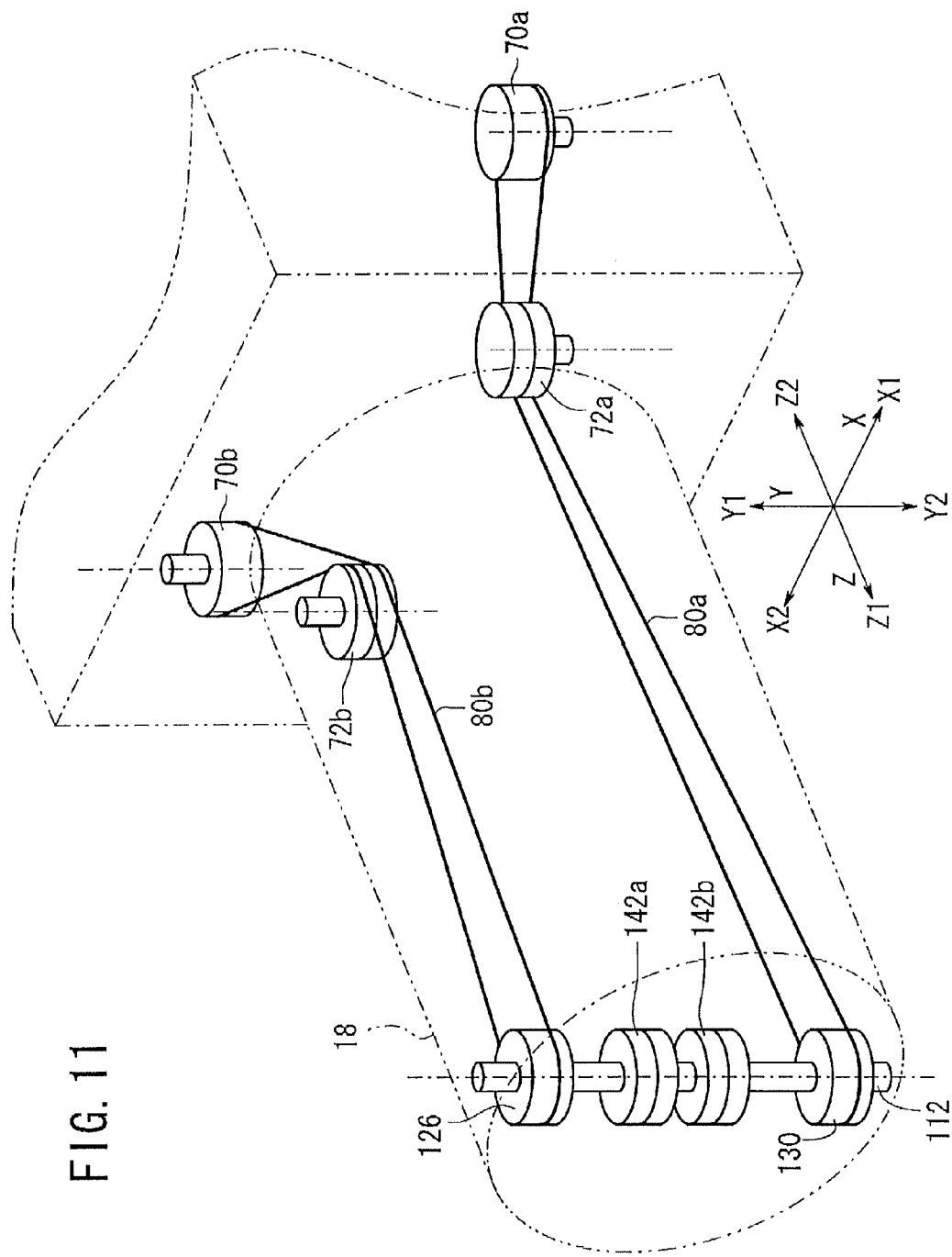
FIG. 11 is a schematic view of a mechanism for transmitting a driving force of a drive unit to a posture change mechanism.

FIG. 11 is a schematic view of a mechanism for transmitting the driving force of the drive unit 30 to the posture change mechanism 13 (refer to FIGS. 6 to 8). As shown in FIG. 11, the above-disclosed shaft 112 (refer to FIGS. 2 and 6) that pivotally supports the guide pulleys 142a and 142b is provided at the tip of the shaft 18, and each of the wires 80a and 80b is wound around a gear body (second rotation body) 126 and a pulley (first rotation body) 130 that are rotatably pivoted through the shaft 112. The gear body 126 and the pulley 130 are components of the posture change mechanism 13.

In the working unit 16, each of wires 80a and 80b is reciprocated between the pulleys 70a and 70b side and the tip operating unit 12 side, and therefore, total four wires 80a and 80b and two rods 82a and 82b are inserted into the hollow space of the shaft 18. For example, all power transmission mechanisms may be configured by only wires instead of the rods. Each of wires 80a and 80b may be the same kind as or different kind from each other, may have the same diameter as or different diameter from each other, and is configured of a bendable wire having flexibility. In the wires 80a and 80b, a linear portion in which the flexibility is not needed in a portion passing through the inner portion of the shaft 18 is surrounded by a reinforcement rod having high stiffness (not shown) and may be reinforced.

A configuration of the tip operating unit 12 will be disclosed in more detail. As shown in FIGS. 5 to 8, the tip operating unit 12 includes the end effector 300, the conversion mechanism 15, and the posture change mechanism 13 which are disclosed above. As disclosed above, the posture change mechanism 13 can perform a roll operation of rotation about the roll axis Or (identical with Z axis at the time of neutral posture) oriented toward the extension direction of the end effector 300 and the yaw operation (tilting operation) of tilting about the yaw axis Oy in the Y direction, and can perform the roll operation and the tilting operation selectively or in combination.

The roll operation through the posture change mechanism 13 is set so as to rotate the end effector 300 about the roll axis Or in the extension direction of the end effector 300, and for example, includes a movable range that is ±180° or equal to or more than ±180°. In addition, the tilting operation through the posture change mechanism 13 is set so as to be swung in the direction that crosses the axial line along the extension direction of the shaft 18, and for example, includes a movable range that is ±90° or equal to or more than ±90°.

The posture change mechanism 13 includes the main shaft member 144 in which the pulley 130 driven to rotate through the first motor 50a via one wire (first transmitting member) 80a and can rotate about the yaw axis (tilt axis) Oy which is not parallel to the axial line of the shaft 18, the gear body 126 that is driven to rotate through the second motor 50b via the other wire (second transmitting member) 80b, and a gear body 146 (third rotation body) that is driven by the gear body 126 and is supported to the main shaft member 144 so as to be rotated about the roll axis Or in the extension direction of the end effector 300.

The gear body 126 and the main shaft member 144 are rotatably supported by the shaft 112 that is provided at the tip of the shaft 18. A pair of protrusion pieces 58 (refer to FIG. 5) that protrude in the Z1 direction is provided in both sides in the Y direction of the tip of the shaft 18, and the shaft 112 is fixed between the pair of protrusion pieces 58 along the Y direction. The gear body 126 includes a barrel 132, and a gear 134 that is concentrically provided on the upper portion of the barrel 132. The pulley 130 has the approximately similar diameter and the approximately similar shape to the barrel 132 of the gear body 126.

A portion of the wires 80a and 80b are fixed to and wound around the pulley 130 and the barrel 132 by predetermined fixing means. For example, an angle through which the wires 80a and 80b are wound is 1.5 rotations (540°). The pulley 130 is integrally provided on the base end side of the main shaft member 144, and the main shaft member 144 is supported to be rotatable (to be tiltable) about the yaw axis through the shaft 122. Accordingly, the pulley 130 is driven to rotate by the wire 80a, and therefore, the main shaft member 144 in which the pulley 130 is integrally provided rotates about the yaw axis Oy.

Two accessory plates 144b and 144b (refer to FIG. 5) that are rotatably supported by the shaft between the pulley 130 and the gear body 126 are provided at the end in the Z2 direction in the main shaft member 144. The accessory plates 144b and 144b are held on the upper surface in the Y direction of the guide pulley 142a and on the lower surface in the Y direction of the guide pulley 142b. In addition, a tubular portion 144d that protrudes from the accessory plates 144b and 144b toward the end effector 300 is provided at the end in the Z1 direction in the main shaft member 144. A square hole 144a that extends in the roll axis Or direction is provided in an axial center portion of the main shaft member 144, the transmitting member 152 which is a component of the above-disclosed conversion mechanism 15 is inserted into the hole 144a, and therefore, the transmitting member 152 is guided so as to advance and retreat in the roll axis direction.

As shown in FIG. 5, a shaft hole 354 in the radial direction to which the pin 352 is inserted and fixed is provided in the main shaft member 144. The shaft hole 354 penetrates the tubular portion 144d of the main shaft member 144 via the hole 144a. In addition, a long hole 356 that extends in the axial direction while having a width at which the pin 352 can be inserted is provided in the transmitting member 152. As shown in FIG. 6, the transmitting member 152 is provided at a position which is slightly offset in the Y1 direction from the roll axis. However, only the protrusion 174 of the tip may be positioned at the axial center. According to an aspect, the transmitting member 152 may be positioned on the roll axis.

The gear body 146 is rotatably supported to the outer circumference of the tubular portion 144d of the main shaft member 144. The gear body 146 to the main shaft member 144 helps prevent the slip-off by a nut body 148. A thrust bearing member 144c made of resin is provided in a portion of the main shaft member 144 that abuts the gear body 146. A thrust bearing member 148a made of resin is provided in a portion of the nut body 148 that abuts the gear body 146. The thrust bearing members 144c and 148a consist of a low friction material, which helps decrease the friction and torque of the abutted portion, and helps prevent a load from being directly applied to a face gear 165.

The thrust bearing members 144c and 148a are a so-called sliding bearing, however, a rolling bearing may be provided. When the gripper 300A is strongly opened or closed, the gear body 146 strongly abuts the main shaft member 144, and the roll operation can be relatively smoothly performed.

The gear body 146 is a tubular shape with a step, and includes a large diameter portion 162 in the Z2 direction, a small diameter portion 164 in the Z1 direction, and the face gear 165 that is provided at the end surface in the Z2 direction of the large diameter portion 162. The face gear 165 engages with the gear 134. A screw portion that screws to a screw portion provided at the end in the Z2 direction side of the tip cover 161 is provided on the outer circumference of the large diameter portion 162.

The base end of the tip cover 161 is connected (screwed or press-fitted) so as to be externally fitted to the gear body 146, and the tip cover 161 and the end effector 300 perform the roll operation according to the rotation of the gear body 146.

In addition, according to the conversion mechanism 15, the posture change mechanism 13, and the tip cover 161 that are disclosed above, a composite mechanism portion 102 that performs the opening and closing operations of the end effector 300 and the posture change of the end effector 300 is configured.

In the posture change mechanism 13 configured as disclosed above, by operating the wires 80b and 80a, the pulley 130 and the gear body 126 can be rotated with respect to the shaft 112. If the pulley 130 is rotated, the tilting operation of the end effector 300 is performed. The main shaft member 144 in which the pulley 130 is integrally provided rotates about the yaw axis Oy, and the gear body 146, the tip cover 161, and the end effector 300 are tilted about the yaw axis Oy so as to be integral with the main shaft member 144.

Alternatively, if the gear body 126 is rotated, the roll operation of the end effector 300 is performed. If the gear body 146 rotates about the roll axis Or by the gear body 126, the tip cover 161 and the end effector 300 rotate about the roll axis Or to be integral with the gear body 146.

As shown in FIG. 12, the composite input unit 24 that electrically drives the tip operating unit 12 has a structure that is symmetrical in the X1 and X2 directions with the Z axis (Y axis) as a center and is a composite input unit that issues a rotation command in the roll direction (axis rotation direction) and the yaw direction (left and right directions) with respect to the tip operating unit 12.

The composite input unit 24 is supported by a sensor holder 88 that is disposed on the inclined plane 26a, and includes a rotation operating unit 90 of the Z1 side (Y1 side) of the inclined plane 26a, a tilting operating unit 92 that is provided at the Z2 side (Y2 side), and three switch operators 94a to 94c that are disposed on the surface of the lower portion side of the tilting operating unit 92, respectively. The operation amount in the input to the rotation operating unit 90 is detected by a switch substrate (not shown) that is provided in the sensor holder 88, and the first and second motors 50a and 50b are appropriately driven and controlled under the control of the controller 29.

With reference to FIGS. 13, 14A, and 14B, a detection mechanism 400 according to a first example will be disclosed. In addition, in descriptions below, the push-out position of the trigger lever 36 means a position at which the trigger lever 36 is sufficiently pushed out (a position in which the trigger lever 36 is most rotated in the Z1 direction side in the movable range of the trigger lever 36) or a position in the vicinity of the position at which the trigger lever 36 is sufficiently pushed out, and the pulling position of the trigger lever 36 means a position in which the trigger lever 36 is sufficiently pulled (a position in which the trigger lever 36 is most rotated in the Z2 direction side in the movable range of the trigger lever 36) or a position in the vicinity of the position at which the trigger lever 36 is sufficiently pulled. In FIG. 13, when the trigger lever 36 is located at the push-out position is shown by a solid line, and when the trigger lever 36 is located at the pulling position is shown by a two-dot chain line.

As shown in FIG. 13, the manipulator 10 according to an aspect further includes the detection mechanism 400 that detects an operation state of the trigger lever 36 which is a first input unit. The detection mechanism 400 according to the first example is configured so as to detect that the trigger lever 36 has reached the pulling position. The detection mechanism 400 detects that the trigger lever 36 reaches the operation position corresponding to a state where the gripper 300A which is the end effector 300 is closed or a state where the gripper is substantially closed.

The detection mechanism 400 includes a protrusion (protrusion piece for detection) 402 that is provided in the trigger lever 36 and a detecting unit 404 that is provided in the operating unit 14. The protrusion 402 is fixed to (is provided in) the arm portion 36a of the trigger lever 36, and in the illustrated example, the protrusion is provided so as to protrude in the Z2 direction and operates along with the trigger lever 36. If the trigger lever 36 swings in the front and rear directions (Z direction), the protrusion 402 also swings with the trigger shaft 39 as a rotation supporting point.

The detecting unit 404 is provided at a position opposite to the end in the Z2 direction side of the lower covers 37a and 37b of the operating unit 14, detects the protrusion 402 in a state where the working unit 16 is mounted on the operating unit 14, and therefore, detects that the trigger lever 36 reaches the above-disclosed pulling position. FIG. 14A is a schematic configuration view when the protrusion 402 and the detecting unit 404 are viewed from the Z2 direction side when the trigger lever 36 is located at the push-out position in FIG. 13. FIG. 14B is a schematic configuration view when the protrusion 402 and the detecting unit 404 are viewed from the Z2 direction side when the trigger lever 36 is located at the pulling position in FIG. 13.

As shown in FIGS. 14A and 14B, a space 405 to which the protrusion 402 can enter and which is concave in the Y1 direction is provided between the left and right upper covers 25a and 25b. The space 405 and an inner portion 19 of the upper covers 25a and 25b are spatially separated from each other by the walls of the upper covers 25a and 25b. The detecting unit 404 includes an operating body 406 that is pressed by the protrusion 402 and moves in the X direction, a tact switch 408 that is pressed by the operating body 406, a switch substrate 409 in which the tact switch 408 is provided, and a switch cover 410 that covers the tact switch 408 and is formed of a flexible material capable of being elastically deformed (for example, silicone rubber).

The operating body 406 is inserted into a hole 412 that is provided in the upper cover 25b and is guided to be movable in the X direction through the hole 412. A locking member 411 is fixed to the outer circumference of the inner portion side of the operating body 406, and the locking member 411 helps prevent the operating body 406 from slipping out to the space 405 side from the upper covers 25a and 25b. A seal member (O-ring in the illustrated example) 413 is disposed between the inner circumferential surface of the hole 412 and the outer circumferential surface of the operating body 406, and the seal member 413 helps prevent penetration of liquid or dust from the space 405 side to the inner portion 19 of the upper covers 25a and 25b. The switch substrate 409 is electrically connected to the controller 29 via the cable 28 (refer to FIG. 13), and signals output from the switch substrate 409 are sent to the controller 29.

A taper surface 403 that is inclined in the X direction is provided in the protrusion 402, the protrusion 402 moves in the Y1 direction, and if the taper surface 403 and one end (end in the X direction) of the operating body 406 abut each other, the operating body 406 is pressed in the X2 direction by the taper surface 403 and moves. In addition, the taper surface that is inclined in the X direction may be provided in one end of the operating body 406, or the taper surface may be provided to both the protrusion 402 and operating body 406.

In the detection mechanism 400 that is configured as disclosed above, when the trigger lever 36 is located at the push-out position, as shown in FIG. 14A, since the protrusion 402 is retreated from the detecting unit 404, the detecting unit 404 does not detect the protrusion 402. Alternatively, if the trigger lever 36 is operated so as to rotate in the Z2 direction and reaches the pulling position, as shown in FIG. 14B, the protrusion 402 presses the operating body 406 and moves the operating body in the X2 direction. Therefore, the tact switch 408 is pressed through the switch cover 410 and detects that the trigger lever 36 has reached the pulling position. Signals corresponding to being pressed are output from the tact switch 408, the signals are sent to the controller 29, and therefore, the trigger lever 36 reaching the pulling position is recognized in the controller 29.

In the manipulator 10 to which the detection mechanism 400 is mounted, whenever the trigger lever 36 reaches the pulling position, the signals from the detecting unit 404 are sent to the controller 29, the frequency is counted, which is stored as use history data for each identification number of the working unit 16. In the manipulator 10, the operation frequency of the trigger lever 36 is detected and stored, and life span prediction of the mechanism (end effector drive mechanism 320) that mechanically transmits a force based on the trigger lever 36 itself or the operation of the trigger lever 36 can be performed using the operation frequency.

In addition, in a case where the controller 29 can be connected to the host computer 31, the controller 29 transmits the signals from the detecting unit 404 to the host computer 31, and the operation frequency of the trigger lever 36 may be stored as the use history data for each identification number of the working unit 16 in the host computer 31.

The detection mechanism 400 shown in FIG. 13 is configured so as to detect that the trigger lever 36 has reached the pulling position. Alternatively, the detection mechanism may be configured so as to detect that the trigger lever 36 reaches the push-out position. Even though the detection mechanism is configured in this way, similar to the above-disclosed that, the operation frequency of the trigger lever 36 is detected, and the life span prediction can be performed.

In the manipulator 10, since the trigger lever 36 reaching the pulling position or the push-out position as an operation state of the trigger lever 36 is detected by the detection mechanism 400, ascertainment and analysis of the operation frequency or the use state of the trigger lever 36 can be performed, and according to the analysis, life span prediction of the mechanism (end effector drive mechanism 320) that mechanically transmits a force based on the trigger lever 36 itself or the operation of the trigger lever 36 can be performed.

In addition, the detection mechanism 400 may be configured so as to detect both when the trigger lever 36 reaches the pulling position and when the trigger lever 36 reaches the push-out position. A second detecting unit having the similar configuration to the above-disclosed detecting unit 404 may be provided at a position where the protrusions 402 can be detected when the trigger lever 36 reaches the push-out position. According to such configuration, the reaching of the trigger lever 36 is detected at a plurality of positions, a more detailed use state can be ascertained, and reliability of the life span prediction is improved.

According to the detection mechanism 400, since the operation of the trigger lever 36 is transmitted to the detecting unit 404 that is provided in the operating unit 14 via the protrusion 402, electronic equipment for detecting the operation angle of the trigger lever 36 need not be provided in the working unit 16. Thus, the working unit 16 can be cleaned relatively easily and sterilized.

In the detection mechanism 400, the protrusion 402 may be provided in the trigger operator 36b, and the detecting unit 404 may be provided in the grip handle 26.

However, as disclosed above, the tip operating unit 12 includes the conversion mechanism 15 that converts the operation of the end effector drive mechanism 320 based on the operation of the trigger lever 36 to the opening and closing operations of the end effector 300, and the posture change mechanism 13 that changes the posture of the end effector 300 by the driving of the drive unit based on the operation of the composite input unit 24. For example, in the state where the trigger lever 36 is pulled up to the pulling position, as shown in FIG. 8, the end effector drive mechanism 320 draws the conversion mechanism 15 in the Z2 direction, and the gear body 146 which is the third rotation body is pressed to the main shaft member 144 in the axial direction (right direction in FIG. 8) via the conversion mechanism 15. As a result, the rotation resistance of the gear body 146 becomes large. In addition, in the state where the trigger lever 36 is pushed out up to the push-out position, as shown in FIG. 7, the end effector drive mechanism 320 presses the conversion mechanism 15 in the Z1 direction, and the gear body 146 which is the third rotation body is pressed to the main shaft member 144 in the axial direction (left direction in FIG. 7) via the conversion mechanism 15. As a result, the rotation resistance of the gear body 146 becomes large.

When the gear body 126 (refer to FIG. 6) is rotated by the wire 80b and the end effector 300 performs the roll operation by rotating the gear body 146 that meshes with the gear body 126, driving torque of the second motor 50b (tension of wire 80b) acts on not only torque that rotates the gear body 146 with the roll axis Or as a center but also driving torque (wire 80a) of the first motor 50a as interference torque. The driving force of the second motor also acts as the torque that rotates the main shaft member 144 with the yaw axis Oy as a center. In addition, the driving torque of the motor 50a (tension of wire 80a) receives the torque that rotates the main shaft member 144 with the yaw axis Oy as a center. When backlash occurs in the driving system related to the driving torque (tension of wire 80a) of the first motor 50a or stiffness of the driving system is not sufficient (for example, elongation of wire), there is a concern that a decrease of trajectory accuracy or positioning accuracy of the tip operating unit 12 may occur due to the interference torque of the mechanism. In order to perform more precise posture control, a control that compensates for the interference torque through a feed forward control may be performed.

When the rotation resistance of the gear body 146 to the main shaft member 144 is decreased, in a state where the end effector 300 does not grip any one, since the interference torque due to the roll operation is decreased, an effect on the tilting operation is decreased. However, when the rotation resistance of the gear body 146 to the main shaft member 144 is increased, in a state where the end effector 300 strongly grips a curved needle for suture, if the gear body 146 is rotated about the roll axis Or for the roll operation, since the interference torque is increased, the effect of the tilting operation is increased.

Accordingly, by detecting a gripping state and a non-gripping state, the control according to the rotation resistance of the gear body 146 with respect to the main shaft member 144, the control according to the interference torque can be performed. In addition, even when the gear body 146 is rotated about the roll axis Or for the roll operation in a state where the end effector 300 is largely and strongly opened, since the interference torque is increased, the effect of the tilting operation is increased.

Therefore, in order to solve the problem in which the tilting operation is generated due to the above-disclosed roll operation, in the manipulator 10 to which the detection mechanism 400 shown in FIG. 13 is mounted, the controller 29 controls the first motor 50a for driving the pulley 130 in order to help prevent or help suppress the generation of the tilting operation due to the roll operation according to the operation state of the trigger lever 36 based on the detection result from the detection mechanism 400.

Specifically, when the controller 29 performs the control for the roll operation, in the case where the trigger lever 36 is positioned at the end of the movable range or the vicinity of the end of the movable range (when the trigger lever 36 is located at the pulling position or the push out position), a compensation control corresponding to the increase of the rotation resistance of the gear body 146 is performed with respect to the first motor 50a for driving the pulley 130 in order to help prevent or help suppress the generation of the tilting operation. In addition, when the trigger lever 36 is positioned at the push out position, the control which is performed by the controller 29 assumes that the detection mechanism 400 is configured so as to detect the trigger lever 36 reaching the push-out position.

When the trigger lever 36 is positioned at positions other than the pulling position or the push-out position, the controller 29 applies a general control command corresponding to the roll operation to the motor 50a. Alternatively, when the trigger lever 36 is located at the pulling position or the push-out position, the controller 29 controls the first motor 50a while adding a corrected value corresponding to the increase of the rotation resistance of the gear body 146 to the general control command value, the effect of the tilting operation is decreased, and only the roll operation is performed. Even when the trigger lever is positioned at positions other than the pulling position or the push out position, since the interference torque is not zero, the corresponding corrected value is added to the control command, and the first motor 50a may be controlled. Thus, even when the rotation resistance of the gear body 146 is increased due to the operation of the trigger lever 36, the trajectory accuracy or the positioning accuracy of the tip operating unit 12 at the time of the roll operation can be effectively improved.

With reference to FIGS. 15A and 15B, a detection mechanism 420 according to a second example will be disclosed. The detection mechanism 420 is similar to the detection mechanism 400 according to the first example in that the detection mechanism 420 includes a protrusion 422 (protrusion piece for detection) that is provided in the trigger lever 36 and a detecting unit 424 that is provided in the operating unit 14, the protrusion 422 is fixed (provided) to the arm portion (refer to FIG. 13) of the trigger lever 36 and is configured so as to detect that the trigger lever 36 has reached the pulling position. The detection mechanism 420 is different from the detection mechanism 400 in the configuration of the detecting unit 424. The detecting unit 424 of the detection mechanism 420 is configured from a photosensor that includes a light projector 424a and a light receiver 424b.

In the detecting unit 424 configured in this way, when the trigger lever 36 is located at the push-out position, as shown in FIG. 15A, since the protrusion 422 is retreated from the detecting unit 424, the detecting unit 424 does not detect the protrusion 422. Alternatively, if the trigger lever 36 is operated so as to rotate in the Z2 direction in FIG. 13 and reaches the pulling position, as shown in FIG. 15B, since the protrusion 422 enters between the light projector 424a and the light receiver 424b and interrupts light from the light projector 424a, the trigger lever 36 reaching the pulling position is detected. The controller 29 recognizes that the light is interrupted, and the trigger lever 36 reaching the pulling position is detected.

In addition, the detection mechanism 420 is configured so as to detect that the trigger lever 36 has reached the pulling position. However, the detection mechanism may be configured so as to detect that the trigger lever 36 reaches the push-out position. In addition, the detection mechanism 420 may be configured so as to detect both when the trigger lever 36 reaches the pulling position and when the trigger lever 36 reaches the push-out position. In the detection mechanism 420, the protrusion 422 may be provided in the trigger operator 36b (refer to FIG. 13), and the detecting unit 424 may be provided in the grip handle 26.

Similar to the manipulator 10 to which the detection mechanism 400 according to the first example is mounted, in the manipulator 10 to which the detection mechanism 420 according to the second example is mounted, the controller 29 (refer to FIG. 13) controls the motor 50a in order to help prevent or help suppress the generation of the tilting operation due to the roll operation according to the operation state of the trigger lever 36 based on the detection result from the detection mechanism 420. Similar to the manipulator 10 to which the detection mechanism 400 according to the first example is mounted, even when the rotation resistance of the gear body 146 is increased due to the operation of the trigger lever 36, the trajectory accuracy or the positioning accuracy of the tip operating unit 12 at the time of the roll operation can be improved relatively effectively.

Figure 16:
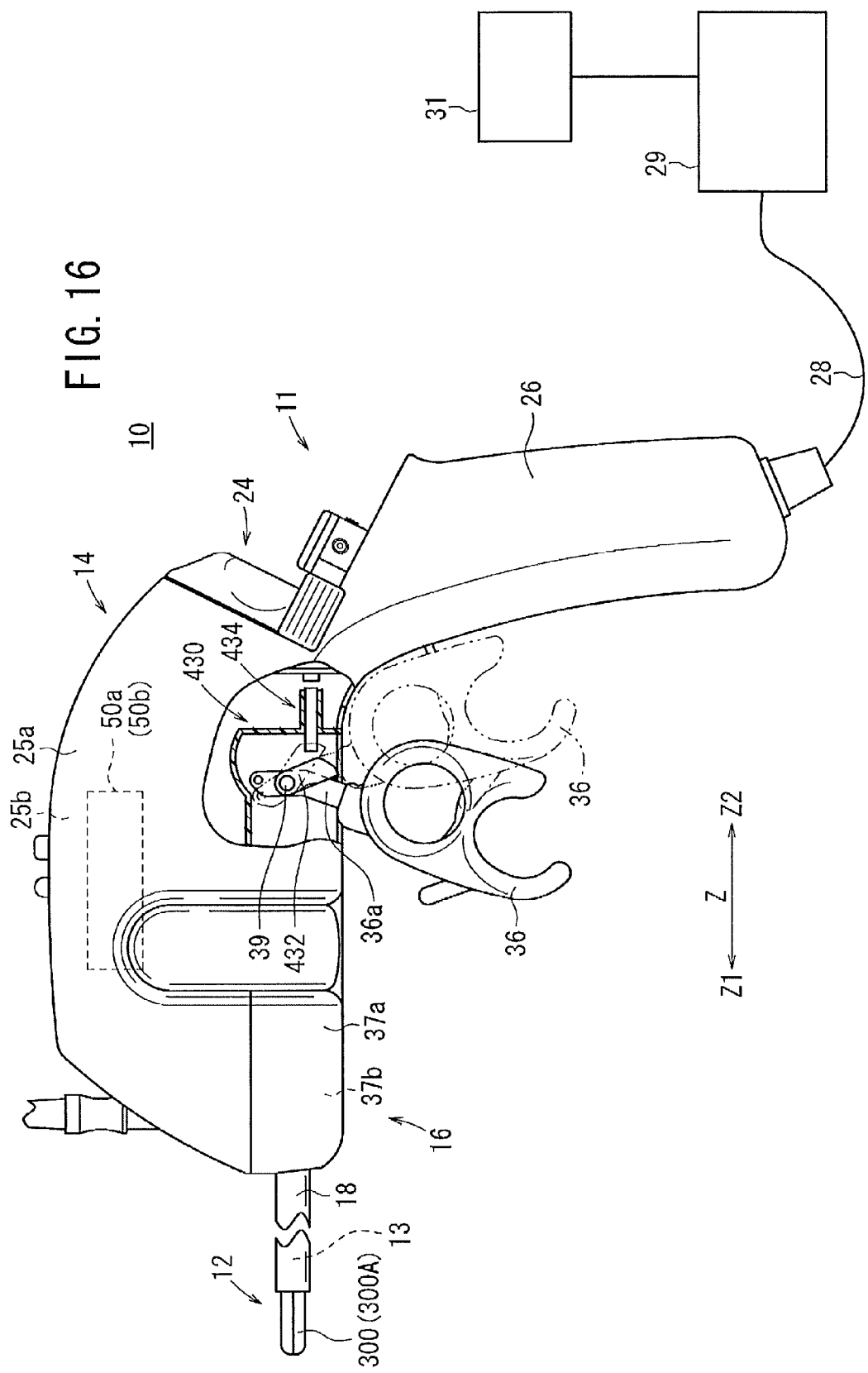
FIG. 16 is a side view in which a portion of the medical manipulator that includes a detection mechanism according to a third example is omitted.
Figure 17A:
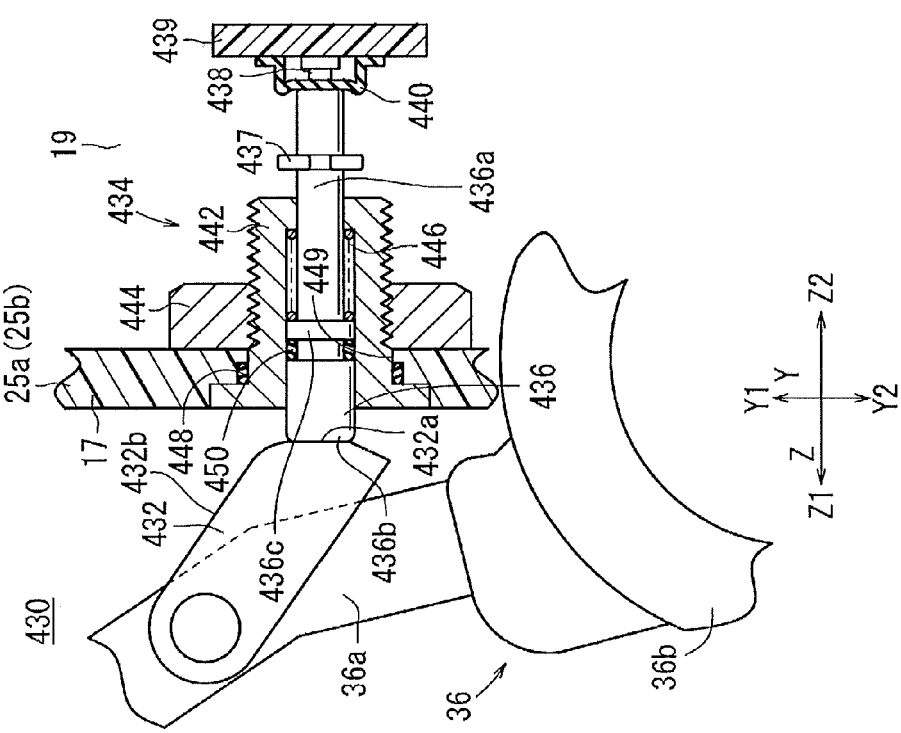
FIG. 17A is a cross-sectional side view of the detection mechanism according to the third example in the state where the trigger lever is pushed out.
Figure 17B:
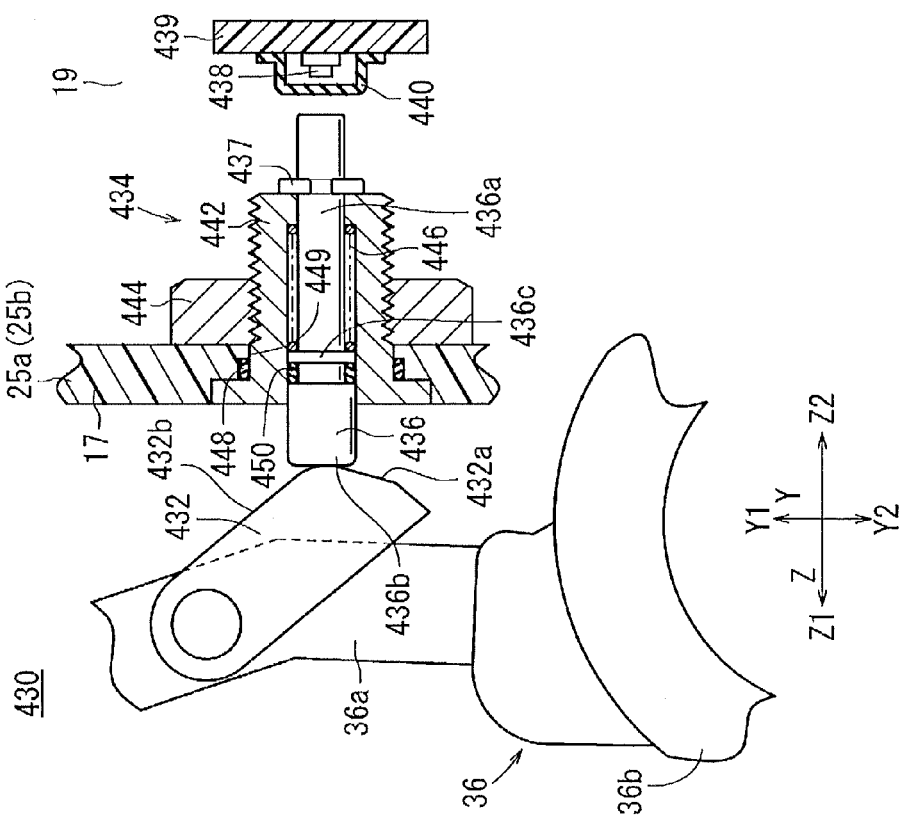
FIG. 17B is a cross-sectional side view of the detection mechanism according to the third example in the state where the trigger lever is pulled.

With reference to FIGS. 16, 17A, and 17B, a detection mechanism 430 according to a third example will be disclosed. In FIG. 16, when the trigger lever 36 is located at the push-out position, the trigger lever 36 is shown by a solid line, and when the trigger lever 36 is located at the pulling position, the trigger lever 36 is shown by a two-dot chain line. As shown in FIG. 16, the detection mechanism 430 according to the third example is configured so as to detect that the trigger lever 36 has reached the pulling position.

The detection mechanism 430 includes a cam body (protrusion piece for detection) 432 that is provided in the trigger lever 36 and a detecting unit 434 that is provided in the operating unit 14. The cam body 432 is fixed to (is provided in) the arm portion of the trigger lever 36, and in the illustrated example, the cam body is provided so as to protrude in the Z2 direction and operates along with the trigger lever 36. If the trigger lever 36 swings in the front and rear directions (Z direction), the cam body 432 also swings with the trigger shaft 39 as a rotation supporting point. In the operating unit 14 in the state where the working unit 16 is mounted on the operating unit 14, the detecting unit 434 is provided at a position opposite to the cam body 432, detects the cam body 432 in the state where the working unit 16 is mounted on the operating unit 14, and therefore, detects that the trigger lever 36 reaches the above-disclosed pulling position.

FIG. 17A is an enlarged configuration view in which a portion of the detection mechanism 430 and the vicinity of the detection mechanism 430 are omitted when the trigger lever 36 is located at the push-out position in FIG. 16. FIG. 17B is an enlarged configuration view in which a portion of the detection mechanism 430 and the vicinity of the detection mechanism 430 are omitted when the trigger lever 36 is located at the pulling position in FIG. 16. As shown in FIGS. 17A and 17B, the detecting unit 434 includes an operating rod 436 that is pressed by the cam body 432 and moves in the Z direction, a cylindrical guide member 442 into which the operating rod 436 is inserted and which guides the movement of the operating body, a tact switch 438 that is pressed by the operating rod 436, a switch substrate 439 in which the tact switch 438 is provided, and a switch cover 440 that covers the tact switch 438 and is formed of a flexible material capable of being elastically deformed (for example, silicone rubber).

The operating rod 436 includes a shaft portion 436a which is inserted into the cylindrical guide member 442 and in which a portion protrudes the tact switch 438 side, and a head portion 436b that is provided in the cam body 432 side rather than the shaft portion 436a and is exposed from a partition 17 which is a portion of the upper covers 25a and 25b to the cam body 432 side. A flange portion 436c is provided on the outer circumference of the shaft portion 436a and a seal member (O-ring in the illustrated example) 450 is disposed between the flange portion 436c and the head portion 436b. The seal member 450 liquid-tightly seals between the outer circumference of the operating rod 436 and the inner circumference of the cylindrical guide member 442.

A coil spring 446 that elastically biases the operating rod 436 toward the cam body 432 side is provided in the inner portion of the cylindrical guide member 442. One end of the coil spring 446 abuts the flange portion 436c of the operating rod 436, and the other end of coil spring 446 abuts a shoulder that is formed in the inner portion of the cylindrical guide member 442. A locking member 437 is fixed to the shaft portion 436b of the operating rod 436, and the locking member 437 helps prevent the operating rod 436 from slipping out to the cam body 432 side from the cylindrical guide member 442.

The cylindrical guide member 442 has a hollow cylindrical shape and is inserted into a hole portion 449 that is provided in the partition 17, and a nut 444 is screwed to a screw portion that is provided on the outer circumference of the cylindrical guide member 442 in the inner portion of the upper covers 25a and 25b. The cylindrical guide member 442 is fixed to the partition 17. A seal member (O-ring in the illustrated example) 448 is disposed between the partition 17 and the cylindrical guide member 442, and the inner circumferential surface of the hole portion 449 and the outer circumferential surface of the cylindrical guide member 442 are liquid-tightly sealed by the seal member 448.

The switch substrate 439 is electrically connected to the controller 29 via the cable, and signals output from the switch substrate 439 are sent to the controller 29. A cam surface 432a that abuts the head portion 436b of the operating rod 436 is provided on the cam body 432. In addition, an inclined portion 432b that is inclined so as to close in the Y2 direction toward the Z2 direction and is continuous to the cam surface 432a is provided on the cam body 432. In FIG. 17A, if the cam body 432 rotates in a counterclockwise direction about the trigger shaft 39, the operating rod 436 is pressed in the Z2 direction by the cam surface 432a and moves against an elastic force of the coil spring 446.

In the detecting unit 434 that is configured as disclosed above, when the trigger lever 36 is located at the push-out position, as shown in FIG. 17A, since the cam body 432 does not insert the operating rod 436 in the Z2 direction, the tact switch 438 is not pressed to the operating rod 436. The trigger lever 36 is rotated in the Z2 direction and reaches the pulling position, as shown in FIG. 17B, since the cam body 432 presses the operating rod 436 and moves in the Z2 direction, and the tact switch 438 is pressed through the switch cover 440 and detects that the trigger lever 36 has reached the pulling position. Signals corresponding to being pressed are output from the tact switch 438, the signals are sent to the controller 29, and therefore, the trigger lever 36 reaching the pulling position is recognized in the controller 29.

In the detection mechanism 430 according to the third example, since the proper inclined portion 432b is provided on the cam body 432, even when the trigger lever 36 is at any angle, the working unit 16 can be mounted on the operating unit 14. Even when the trigger lever 36 is located at the pulling position, the working unit 16 is mounted on the operating unit 14, the tip of the operating rod 436 contacts the inclined portion 432b of the cam body 432 and is inserted in the Z2 direction, and at the time of the mounting completion, the trigger lever 36 being located at the pulling position can be detected.

The detection mechanism 430 of the illustrated example is configured so as to detect that the trigger lever 36 has reached the pulling position. However, the detection mechanism may be configured so as to detect that the trigger lever 36 has reached the push-out position. In addition, the detection mechanism 430 may be configured so as to detect both when the trigger lever 36 reaches the pulling position and when the trigger lever 36 reaches the push-out position. In the detection mechanism 430, the cam body 432 may be provided in the trigger operator 36b, and the detecting unit 434 may be provided in the grip handle 26.

In the manipulator 10 to which the detection mechanism 430 is mounted, whenever the trigger lever 36 reaches the pulling position (or the push-out position), the signals from the detecting unit 434 are sent to the controller 29, the frequency is counted, which is stored as use history data for each identification number of the working unit 16. In addition, in a case where the controller 29 can be connected to the host computer 31, the controller 29 transmits the signals from the detecting unit 434 to the host computer 31, and the operation frequency of the trigger lever 36 may be stored as the use history data for each identification number of the working unit 16 in the host computer 31.

According to the detection mechanism 430, the trigger lever 36 reaching the pulling position or the push-out position as the operation state of the trigger lever 36 is detected. Accordingly, similar to the manipulator 10 that includes the detection mechanism 400 according to the first configuration example, ascertainment and analysis of the operation frequency of the trigger lever 36 and the life span prediction of the end effector drive mechanism 320 can be performed.

According to the detection mechanism 430, since the operation of the trigger lever 36 is transmitted to the detecting unit 434 that is provided in the operating unit 14 via the cam body 432, electronic equipment for detecting the operation angle of the trigger lever 36 need not be provided in the working unit 16. Thus, the working unit 16 can be cleaned relatively easily and sterilized.

In the detection mechanism 430, since the seal members 448 and 450 seal between the partition 17 and the cylindrical guide member 442 and between the cylindrical guide member 442 and the operating rod 436 respectively, which helps prevent penetration of liquid or dust from the trigger lever 36 side to the inner portion 19 of the upper covers 25a and 25b.

Similar to the manipulator 10 to which the detection mechanism 400 according to the first configuration example is mounted, in the manipulator 10 to which the detection mechanism 430 according to the third example is mounted, the controller 29 (refer to FIG. 16) controls the first motor 50a in order to help prevent or help suppress the generation of the tilting operation due to the roll operation according to the operation state of the trigger lever 36 based on the detection result from the detection mechanism 430. Thus, similar to the manipulator 10 to which the detection mechanism 400 according to the first example is mounted, even when the rotation resistance of the gear body 146 is increased due to the operation of the trigger lever 36, the trajectory accuracy or the positioning accuracy of the tip operating unit 12 at the time of the roll operation can be effectively improved.

Next, with reference to FIGS. 18A and 18B, a detection mechanism 430a according to a fourth example will be disclosed. The detection mechanism 430a is similar to the detection mechanism 430 according to the third example in that the detection mechanism 430a includes the cam body 432 (protrusion piece for detection) that is provided in the trigger lever 36 and a detecting unit 434a that is provided in the operating unit 14, the cam body 432 is fixed (is provided) to the arm portion 36a (refer to FIG. 16) of the trigger lever 36 and is configured so as to detect that the trigger lever 36 has reached the pulling position. The detecting unit 434a of the detection mechanism 430a is not a tact switch, and includes a photosensor 460 that is configured of a light projector 460a and a light receiver 460b.

In the detecting unit 434a configured in this way, when the trigger lever 36 is located at the push-out position, as shown in FIG. 18A, since the cam body 432 does not insert the operating rod 436 in the Z2 direction, the operating rod 436 does not interrupt the light from the light projector 460a. If the trigger lever 36 is operated so as to rotate in the Z2 direction and reaches the pulling position, as shown in FIG. 18B, since the protrusion enters between the light projector 460a and the light receiver 460b and interrupts light from the light projector 460a, the trigger lever 36 reaching the pulling position is detected. The controller 29 recognizes that the light is interrupted, and the trigger lever 36 reaching the pulling position is detected.

In the detection mechanism 430a according to the fourth example, since the proper inclined portion 432b is provided on the cam body 432, even when the trigger lever 36 is at any angle, the working unit 16 can be mounted on the operating unit 14. Even when the trigger lever 36 is located at the pulling position, the working unit 16 is mounted on the operating unit 14, the tip of the operating rod 436 contacts the inclined portion 432b of the cam body 432 and is inserted in the Z2 direction, and at the time of the mounting completion, the trigger lever 36 being located at the pulling position can be detected.

The detection mechanism 430a of the illustrated example is configured so as to detect that the trigger lever 36 has reached the pulling position. Alternatively, the detection mechanism may be configured so as to detect that the trigger lever 36 has reached the push-out position. In addition, the detection mechanism 430a may be configured so as to detect both when the trigger lever 36 reaches the pulling position and when the trigger lever 36 reaches the push-out position. In the detection mechanism 430a, the cam body 432 may be provided in the trigger operator 36b, and the detecting unit 434a may be provided in the grip handle 26.

According to the detection mechanism 430a, the trigger lever 36 reaching the pulling position or the push-out position as the operation state of the trigger lever 36 is detected. Accordingly, similar to the manipulator 10 that includes the detection mechanism 400 according to the first example, ascertainment and analysis to the operation frequency of the trigger lever 36, and the life span prediction of the end effector drive mechanism 320 can be performed.

According to the detection mechanism 430a, since the operation of the trigger lever 36 is transmitted to the detecting unit 434a that is provided in the operating unit 14 via the cam body 432, electronic equipment for detecting the operation angle of the trigger lever 36 need not be provided in the working unit 16. Thus, the working unit 16 can be cleaned relatively easily and sterilized.

Similar to the manipulator 10 to which the detection mechanism 400 according to the first example is mounted, in the manipulator 10 to which the detection mechanism 430a according to the fourth example is mounted, the controller 29 (refer to FIG. 16) controls the motor 50a in order to help prevent or help suppress the generation of the tilting operation due to the roll operation according to the operation state of the trigger lever 36 based on the detection result from the detection mechanism 430a. Similar to the manipulator 10 to which the detection mechanism 400 according to the first example is mounted, even when the rotation resistance of the gear body 146 is increased due to the operation of the trigger lever 36, the trajectory accuracy or the positioning accuracy of the tip operating unit 12 at the time of the roll operation can be effectively improved.

In the detection mechanisms 400, 420, 430, and 430a according to the first to fourth examples, the tact switch or the photosensor is used as the detection means of the detecting unit. However, other detection means such as a magnetic sensor and a proximity sensor may be used.

Figure 19:
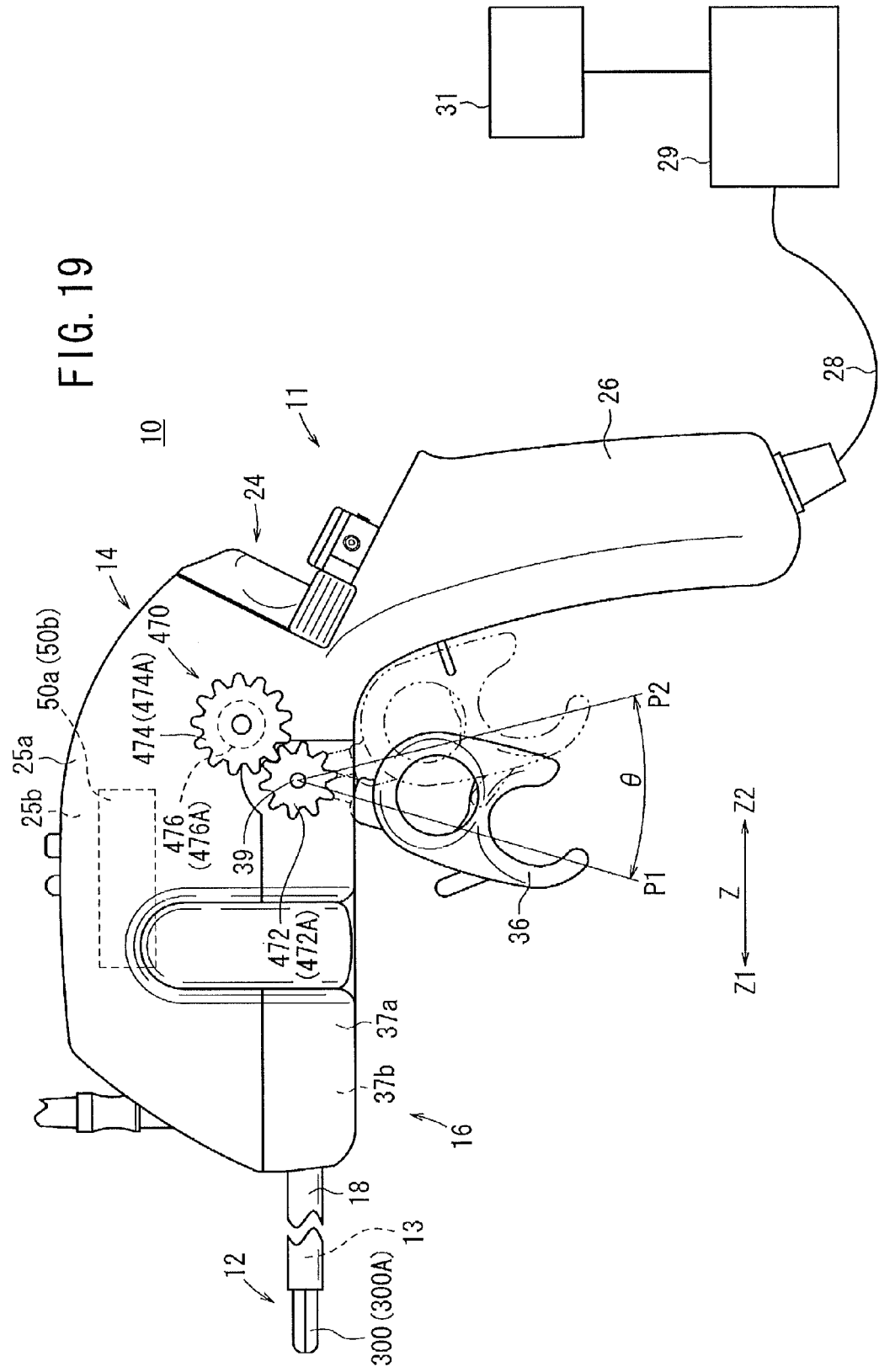
FIG. 19 is a side view in which a portion of the medical manipulator that includes a detection mechanism according to a fifth example is omitted.
Figure 20:
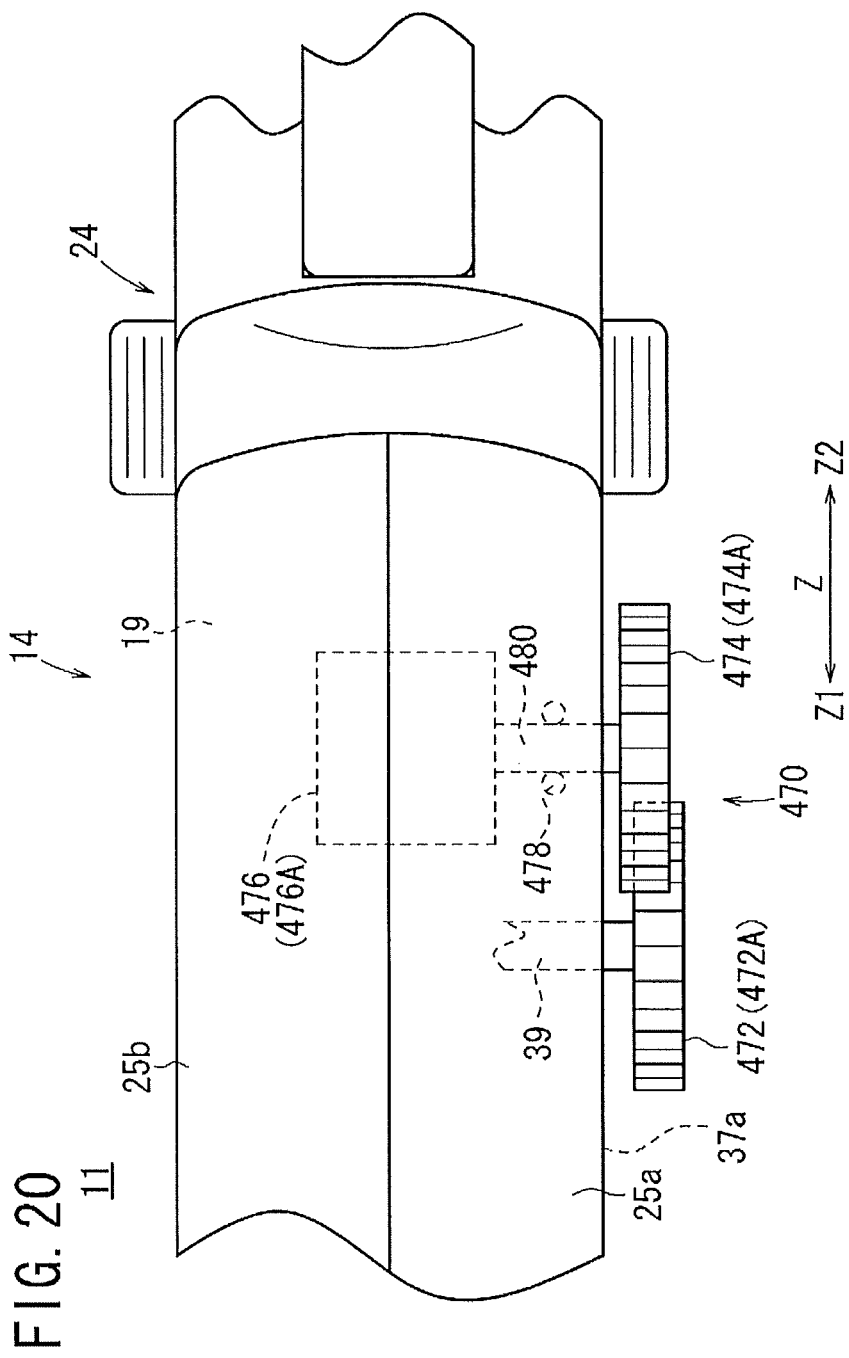
FIG. 20 is a plan view in which a portion of the medical manipulator that includes the detection mechanism according to the fifth example is omitted.

With reference to FIGS. 19 and 20, a detection mechanism 470 according to a fifth example will be disclosed. FIG. 19 is a side view of the manipulator 10 that includes the detection mechanism 470. FIG. 20 is a plan view in which a portion of the manipulator 10 that includes the detection mechanism 470 is omitted. The detection mechanism 470 according to the fifth example is configured so as to detect the operation direction of the trigger lever 36, the position in the rotation direction. As shown in FIG. 19, the trigger lever 36 includes a movable range of an angle θ from the most advance position P1 in which the trigger lever is most rotated in the Z1 side to the most retreat position P2 in which the trigger lever is most rotated in the Z2 side.

The detection mechanism 470 includes a drive element 472 that is operated along with the trigger lever 36, a driven element 474 that operates in conjunction with the drive element 472 in the state where the working unit 16 provided in the operating unit 14 is mounted on the operating unit 14, and a detecting unit 476 that detects the position in the operation direction of the driven element 474. In the illustrated example, the drive element 472 is a first gear portion 472A that includes teeth extending in the circumferential direction around the rotation axial center of the trigger lever 36, the driven element 474 is a second gear portion 474A that is rotatably provided in the operating unit 14 and meshes with the first gear portion 472A in the state where the working unit 16 is mounted on the operating unit 14, and the detecting unit 476 is a rotation detector 476A that detects the rotation angle of the second gear portion 474A.

As shown in FIG. 20, the first gear portion 472A is provided so as to rotate along with the trigger lever 36. The first gear portion 472A is fixed to the trigger shaft 39 that rotates along with the trigger lever 36, and if the trigger lever 36 rotates in the front and rear direction (Z direction), the first gear portion 472A also rotates with the trigger shaft 39 as a rotation supporting point. In addition, in the first gear portion 472A of the illustrated example, the teeth are formed on the entire circumference. However, if the first gear portion can mesh with the second gear portion 474A over the entire movable range of the trigger lever 36, the teeth can be formed on only a portion of the outer circumference.

The second gear portion 474A is provided in the side surface of the upper cover 25b. The rotation detector 476A is provided in the inner portion 19 of the upper covers 25a and 25b. The second gear portion 474A and the rotation detector 476A are connected to each other via a shaft 480 that penetrates the upper covers 25a and 25b. A seal member (O-ring in the illustrated example) 478 is disposed between the upper covers 25a and 25b and the shaft, and the seal member 478 helps prevent entering of the liquid or dust from the outside to the inner portion 19 of the upper covers 25a and 25b.

For example, as the rotation detector 476A, a rotary encoder, a potentiometer, or a resolver may be used. An incremental encoder and an absolute encoder may be used as the rotary encoder, and any encoder may be used. The rotation detector 476A is electrically connected to the controller 29 via the cable 28, and signals output from the rotation detector 476A are sent to the controller 29.

In the detection mechanism 470 that is configured as disclosed above, if the trigger lever 36 is operated to rotate, the first gear portion 472A provided in the trigger lever 36 rotates about the trigger shaft 39 so as to be integral with the trigger lever 36. In addition, according to the rotation of the first gear portion 472A, the second gear portion 474A that meshes with the first gear portion 472A rotates, the rotation angle of the second gear portion 474A is detected through the rotation detector 476A, and the operation angle of the trigger lever 36 is detected. Signals corresponding to the rotation angle are output from the rotation detector 476A, the signals are transmitted to the controller 29, and the operation angle of the trigger lever 36 is calculated based on the signals from the rotation detector 476A.

In addition, when the rotation detector 476A is the incremental encoder, only pulses corresponding to the change of the rotation angle are output from the incremental encoder, and the absolute angle of the trigger lever 36 cannot be directly detected. Since the movable range (maximum rotation angle) θ of the trigger lever 36 is already known, it is possible to estimate the absolute angle of the trigger lever 36 from the rotation angle range at the time of use. Therefore, when the rotation detector 476A is the incremental encoder, the controller 29 estimates (calculates) the absolute angle of the trigger lever 36 based on the movable range θ of the trigger lever 36 and the rotation angle range detected by the rotation detector 476A at the time of the use of the manipulator 10. Since the absolute angle of the trigger lever 36 is estimated from the detected signals of the incremental encoder, the detection of the operation angle of the trigger lever 36 can be performed through the simple configuration.

In the manipulator 10 to which the detection mechanism 470 is mounted, the operation angle of the trigger lever 36 is detected for each predetermined sampling timing during the use of the manipulator 10, which is stored as use history data for each identification number of the working unit 16. In the manipulator 10, the operation frequency or the use state of the trigger lever 36 is detected and stored, and life span prediction of the mechanism (end effector drive mechanism 320) (refer to FIG. 2) that mechanically transmits a force based on the trigger lever 36 itself or the operation of the trigger lever 36 can be performed using the operation frequency or the use state. For example, according to the detection mechanism 470 according to the fifth configuration example, since the operation angle of the trigger lever 36 is detected, compared to the detection mechanisms 400, 420, 430, and 430a according to the first to fourth examples, one can ascertain the use state of the trigger lever 36 in more detail, and the reliability of the life span prediction is improved.

In addition, in the case where the controller 29 can be connected to the host computer 31, the controller 29 transmits the signals from the detecting unit 476 to the host computer 31, and the operation frequency or the use state of the trigger lever 36 may be stored as the use history data for each identification number of the working unit 16 in the host computer 31.

According to the detection mechanism 470, since the operation of the trigger lever is transmitted to the detecting unit 404 that is provided in the operating unit 14 via the protrusion 402, electronic equipment for detecting the operation position of the trigger lever 36 need not be provided in the working unit 16. The working unit 16 can be cleaned relatively easily and sterilized.

Similar to the manipulator 10 to which the detection mechanism 400 according to the first configuration example is mounted, in the manipulator 10 to which the detection mechanism 470 according to the fifth example is mounted, the controller 29 controls the first motor 50a in order to help prevent or help suppress the generation of the tilting operation due to the roll operation according to the operation state of the trigger lever 36 based on the detection result from the detection mechanism 470.

When the controller 29 observes the operation angle of the trigger lever 36 based on the detection result of the detection mechanism 470 and performs the control for the roll operation, in the case where the trigger lever 36 is located at the push out position (P1 or the vicinity of the push out position) or the pulling position (P2 or the vicinity of the pulling position), the compensation control corresponding to the increase of the rotation resistance of the gear body 146 (refer to FIGS. 6 and 7) is performed with respect to the first and second motors 50a and 50b helps prevent or helps suppress the generation of the tilting operation.

Similar to the manipulator 10 to which the detection mechanism 400 according to the first configuration example is mounted, according to the manipulator 10 to which the detection mechanism 470 according to the fifth example is mounted, even when the rotation resistance of the gear body 146 is increased due to the operation of the trigger lever 36, the trajectory accuracy or the positioning accuracy of the tip operating unit 12 at the time of the roll operation can be improved relatively effectively.

As shown in FIGS. 19 and 20, the rotation axial center of the trigger lever 36 and the rotation axial center of the second gear portion 474A, for example may be positioned so as to be off-set from each other in the extension direction (Z direction) of the shaft in the state where the working unit 16 is mounted on the operating unit 14. According to this configuration, when the working unit 16 is mounted on the operating unit 14, since the first gear portion 472A provided in the working unit 16 and the second gear portion 474A provided in the operating unit 14 are off-set from each other in the Z direction, a meshing operation between the first gear portion 472A and the second gear portion 474A can be relatively smoothly performed. Thus, the mounting operation of the working unit 16 on the operating unit 14 can be relatively smoothly performed.

In addition, a magnetic coupling may be adopted as the mechanism that transmits the rotation of the trigger lever 36 to the rotation detector 476A. At least one of the drive element 472 provided in the trigger lever 36 and the driven element 474 provided in the operating unit 14 is configured to a disk on which a permanent magnet is disposed, the other one is configured to a disk on which a permanent magnet is disposed or a disk that is formed of a ferromagnetic body, and the magnetic coupling may be configured of the drive element 472 and the driven element 474 that are configured as disclosed above. Also according to the magnetic coupling, since electronic equipment for detecting the operation position of the trigger lever 36 need not be provided in the working unit 16, the working unit 16 can be cleaned relatively easily and sterilized.

Figure 21:
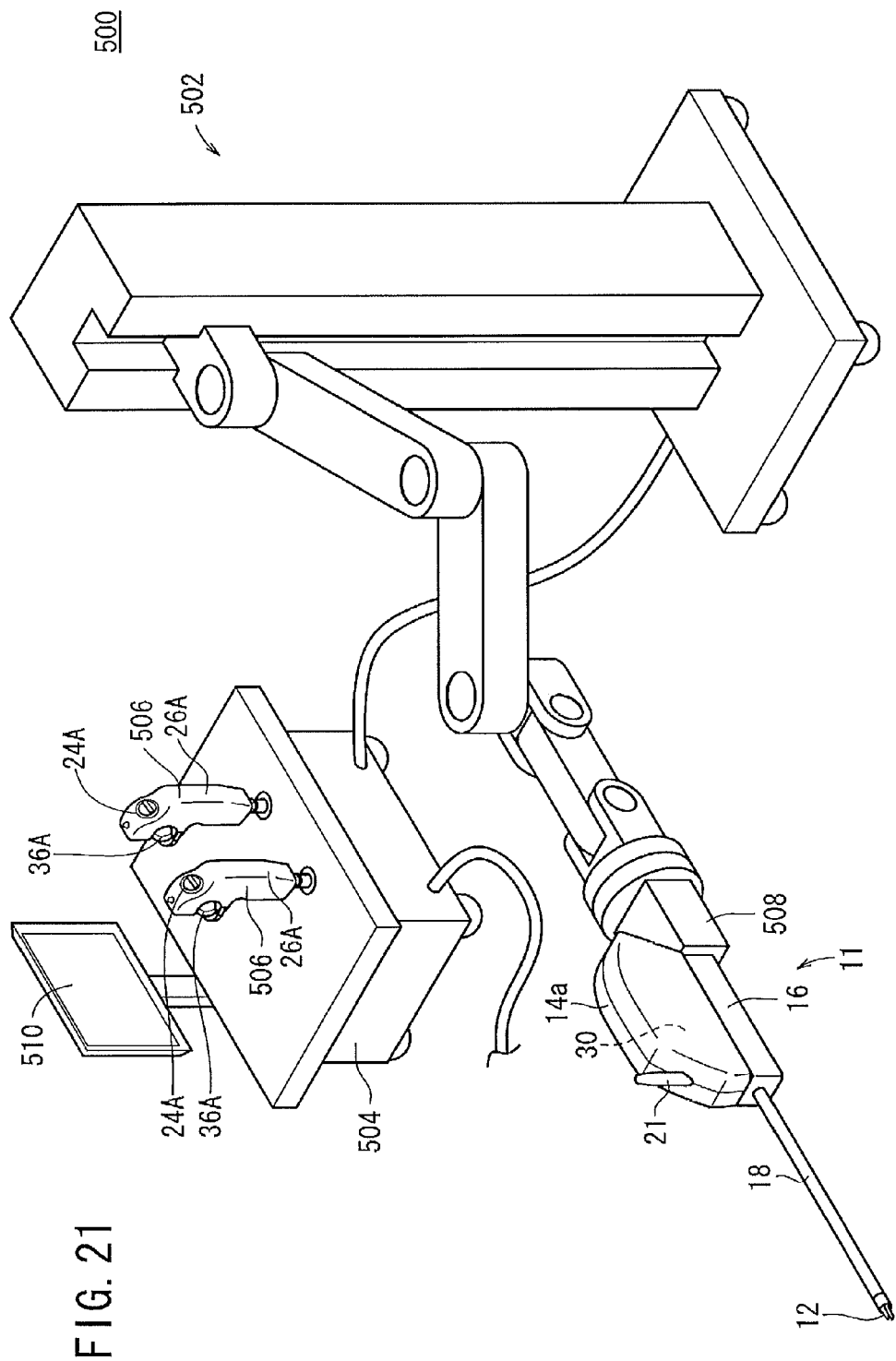
FIG. 21 is a schematic perspective view of a robot system for surgery.

For example, the medical manipulator as disclosed can be applied to a robot system for surgery 500 shown in FIG. 21. The robot system for surgery 500 includes a multiple joint type robot arm 502 and a console 504 that controls the robot arm, and a mechanism similar to the manipulator main body 11 is provided at the tip of the robot arm 502. A base portion 14a that accommodates the drive mechanism 30 in the inner portion instead of the operating unit 14 is fixed to the tip 508 of the robot arm 502, and the working unit 16 in which the tip operating unit 12 is provided is mounted so as to be attached to and detached from the base portion 14a.

The robot arm 502 may be any means for moving the working unit 16, is not limited to a stationary type, and for example may be autonomously mobile type. If the robot arm 502 includes 6 or more joints (rotation shafts or slide shafts) that are independent to each other, since the position and the direction of the working unit 16 can be arbitrarily set. The base portion 14a configuring the manipulator main body 11 of the tip is integrated with the tip 508 of the robot arm 502.

In the console 504, two joysticks 506 and a monitor 510 which are an operation command unit are provided. The console 504 may adopt a configuration such as a table type or control panel type. The robot arm 502 is operated under the operation of the console 504, and an automatic operation through a program, an operation according to the joysticks 506 provided in the console 504, or the composite operations of the robot arm 502 and the joysticks 506 may be configured. The console 504 includes the functions of the controller 29.

According to two joysticks 506, two robot arms 502 can be individually operated. In addition, in FIG. 21, a single robot arm 502 is shown. Two joysticks 506 are provided at a position where an operation is performed relatively easily with both hands. The joysticks 506 may perform up and down operations, left and right operations, a twist operation, and a tilting operation, and move the robot arm 502 according to these operations. The joysticks 506 may be a master arm.

A grip handle 26A, a trigger lever 36A that is operated to be pulled and pushed, and a composite operation unit 24A that is operated to be rotated and be tilted are provided in the joy sticks 506. The trigger lever 36A is a substitute for the trigger lever 36 (refer to FIG. 1), the trigger lever 36A is operated, and the two rods 82a and 82b (refer to FIG. 2 and not shown in FIG. 21) can be driven to advance and retreat through a motor (not shown) (actuator that drives in conjunction with the input unit operated by hands). The composite operation unit 24A is a substitute for the composite input unit 24 (refer to FIG. 12). The composite operation unit 24A is operated by the drive unit 30, which is controlled by the console 504 according to the content of the operation, the roll operation, and the tilting operation, or the composite operation of the content of the operation, the roll operation and the tilting operation of the tip operating unit 12, which is being performed.

Communication means between the robot arm 502 and the console 504 may be made by wire, wireless, networks, or a combination thereof. The information on an image can be displayed on the monitor 510 through a flexible mirror.

The detailed description above discloses a medical manipulator and manner of using the medical manipulator. The invention is not limited, however, to the embodiments and variations disclosed above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical manipulator comprising:
  a working unit that includes:
    a body;
    a first input unit extending from the body and configured to be operated by hands;
    a shaft that extends from the body;
    a tip operating unit that is provided at a tip of the shaft and includes an end effector to which an operation of the first input unit is mechanically transmitted and in which the operation is performed;
    wherein the tip operating unit includes a posture change mechanism configured to change a posture of the end effector with respect to the shaft; and
  an operating unit removably mounted on the working unit, the operating unit including:
    a second input unit configured to be operated by hands;
    a grip handle configured to be gripped by hands; and
    a drive source configured to drive the posture change mechanism of the tip operating unit based on an operation of the second input unit;
  wherein the first input unit of the working unit includes a protrusion piece and the operating unit includes a detecting unit, the protrusion piece and the detecting unit being components of a detection mechanism configured to detect an operation state of the first input unit, and the protrusion piece configured to press the detecting unit to detect the operation state of the first input unit;
  wherein the working unit and the operating unit are discrete components relative to one another, and are configured to permit relatively smooth mounting of the operating unit on the working unit.

2. The medical manipulator of claim 1, wherein the detection mechanism is configured to detect that the first input unit reaches a predetermined position.

3. The medical manipulator of claim 2, further comprising:
  a driving force of the drive source is mechanically transmitted to the posture change mechanism in a state where the working unit is mounted on the operating unit, which changes a posture of the end effector; and the detecting unit configured to detect the protrusion piece for detection in the state where the working unit is mounted on the operating unit, and configured to detect that the first input unit reaches the predetermined position.

4. The medical manipulator of claim 1, wherein the detection mechanism is configured to detect that the first input unit reaches a predetermined position at each of a plurality of predetermined positions in a movable range of the first input unit.

5. The medical manipulator of claim 1, wherein the tip operating unit includes a conversion mechanism configured to convert an operation based on the operation of the first input unit to an operation of the end effector.

6. The medical manipulator of claim 5, wherein the posture change mechanism comprises:
a main shaft member in which a first rotation body that is configured to be rotated by a first actuator via a first transmitting member inserted into the shaft is provided and which can rotate about a tilt shaft which is non-parallel to an axial line of the shaft, a second rotation body that is configured to be rotated by a second actuator via a second transmitting member inserted into the shaft, and a third rotation body that is configured to be driven by the second rotation body and is supported to the main shaft member to rotate about a roll axis in an extension direction of the end effector;
the main shaft member driven by the first transmitting member rotates about the tilt shaft performing a tilting operation of the end effector; and
the second rotation body driven by the second transmitting member rotates the third rotation body about the roll axis performing a roll operation of the end effector.

7. The medical manipulator of claim 6, further comprising:
a controller configured to control the first actuator and the second actuator, and the controller configured to control the first actuator to suppress the generation of the tilting operation due to the roll operation according to an operation state of the first input unit based on a detection result from the detection mechanism.

8. The medical manipulator of claim 7, wherein the end effector is configured of an opening and closing mechanism.

9. The medical manipulator of claim 8, wherein the controller is configured to perform the control for the roll operation when the first input unit is positioned at the end of a movable range, and a compensation control corresponding to the increase of the rotation resistance of the third rotation body is performed with respect to the first actuator to suppress the generation of the tilting operation.

10. The medical manipulator of claim 1, wherein the first input unit is moveable between a first position and a second position.

11. The medical manipulator of claim 1, wherein the protrusion piece is fixed to the first input unit.

12. A medical manipulator comprising:
a working unit that includes:
a body;
a trigger lever extending from the body and configured to be operated by hands;
a shaft that extends from the body;
a tip operating unit that is provided at a tip of the shaft and includes an end effector to which an operation of the trigger lever is mechanically transmitted and in which the operation is performed;
wherein the tip operating unit includes a posture change mechanism configured to change a posture of the end effector with respect to the shaft; and
an operating unit removably mounted on the working unit, the operating unit including:
a second input unit configured to be operated by hands;
a grip handle configured to be gripped by hands; and
a drive source configured to drive the posture change mechanism based on an operation of the second input unit;
wherein the trigger lever of the working unit includes a protrusion piece and the operating unit includes a detecting unit, the protrusion piece and the detecting unit being components of a detection mechanism configured to detect an operation state of the trigger lever; and the protrusion piece configured to press the detecting unit to detect the operation state of the trigger lever;
wherein the working unit and the operating unit are discrete components relative to one another, and are configured to permit relatively smooth mounting of the operating unit on the working unit.

13. The medical manipulator of claim 12, wherein the detection mechanism is configured to detect that the trigger lever reaches a predetermined position.

14. The medical manipulator of claim 13, further comprising:
a driving force of the drive source is mechanically transmitted to the posture change mechanism in a state where the working unit is mounted on the operating unit, which changes a posture of the end effector; and
the detecting unit configured to detect the protrusion piece for detection in the state where the working unit is mounted on the operating unit, and configured to detect that the trigger lever reaches the predetermined position.

15. The medical manipulator of claim 12, wherein the trigger lever is moveable between a push-out position and a pulling position.

16. The medical manipulator of claim 12, wherein the protrusion piece is fixed to the trigger lever.

* * * * *